(12) United States Patent
Little et al.

(10) Patent No.: US 12,150,994 B2
(45) Date of Patent: Nov. 26, 2024

(54) BIOMIMETIC DRUG DELIVERY OF AN IMMUNOMODULATORY AGENT FOR THE TREATMENT OF OCULAR CONDITIONS

(71) Applicant: University of Pittsburgh—Of the Commonwealth System of Higher Education, Pittsburgh, PA (US)

(72) Inventors: Steven R. Little, Allison Park, PA (US); Michelle L. Guaragno, Carnegie, PA (US); Andrew J. Glowacki, Pittsburgh, PA (US); Morgan V. Fedorchak, Mars, PA (US); Stephen C. Balmert, Cranberry Township, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 270 days.

(21) Appl. No.: 17/834,597

(22) Filed: Jun. 7, 2022

(65) Prior Publication Data
US 2022/0296716 A1 Sep. 22, 2022

Related U.S. Application Data

(62) Division of application No. 15/628,233, filed on Jun. 20, 2017, now Pat. No. 11,395,853.

(60) Provisional application No. 62/353,908, filed on Jun. 23, 2016.

(51) Int. Cl.
| | | |
|---|---|---|
| *A61K 38/18* | (2006.01) | |
| *A61K 9/00* | (2006.01) | |
| *A61K 9/50* | (2006.01) | |
| *A61K 31/436* | (2006.01) | |
| *A61K 39/39* | (2006.01) | |
| *A61K 45/06* | (2006.01) | |
| *A61P 27/02* | (2006.01) | |
| *A61P 27/04* | (2006.01) | |
| *A61K 38/20* | (2006.01) | |
| *A61K 39/00* | (2006.01) | |

(52) U.S. Cl.
CPC ............ *A61K 45/06* (2013.01); *A61K 9/0048* (2013.01); *A61K 9/5031* (2013.01); *A61K 31/436* (2013.01); *A61K 39/39* (2013.01); *A61P 27/02* (2018.01); *A61P 27/04* (2018.01); *A61K 38/1841* (2013.01); *A61K 38/2013* (2013.01); *A61K 2039/55555* (2013.01)

(58) Field of Classification Search
CPC .................................................. A61K 38/195
See application file for complete search history.

(56) References Cited

U.S. PATENT DOCUMENTS

| | | |
|---|---|---|
| 5,837,226 A | 11/1998 | Jungherr et al. |
| 6,264,971 B1 | 7/2001 | Darougar et al. |
| 6,656,460 B2 | 12/2003 | Benita et al. |
| 7,060,299 B2 | 6/2006 | Alavattam et al. |
| 7,589,057 B2 | 9/2009 | Chang et al. |
| 8,298,569 B2 | 10/2012 | Philips et al. |
| 8,410,168 B2 | 4/2013 | Widder et al. |
| 8,492,334 B2 | 7/2013 | Lavik et al. |
| 9,018,006 B2 | 4/2015 | Stepkowski et al. |
| 9,056,045 B2 | 6/2015 | Hughes et al. |
| 2002/0197300 A1 | 12/2002 | Schultz et al. |
| 2006/0173060 A1 | 8/2006 | Chang et al. |
| 2006/0246145 A1 | 11/2006 | Chang et al. |
| 2009/0252781 A1 | 10/2009 | Sawheney et al. |
| 2010/0209478 A1 | 8/2010 | Sawheny et al. |
| 2010/0261646 A1 | 10/2010 | Lavik et al. |
| 2011/0189291 A1 | 8/2011 | Yang et al. |
| 2011/0206773 A1 | 8/2011 | Lavik et al. |
| 2012/0148676 A1 | 6/2012 | Little |
| 2012/0156176 A1 | 6/2012 | Fujimoto et al. |
| 2012/0231072 A1 | 9/2012 | Kang-Mieler et al. |
| 2013/0122064 A1 | 5/2013 | Ahlheim et al. |
| 2014/0086975 A1 | 3/2014 | Sinko et al. |
| 2015/0037422 A1 | 2/2015 | Kaplan et al. |
| 2015/0297662 A1 | 10/2015 | Betts et al. |
| 2015/0374633 A1 | 12/2015 | Fedorchak et al. |

FOREIGN PATENT DOCUMENTS

| | | |
|---|---|---|
| WO | WO 2011/106702 | 9/2011 |
| WO | WO 2012/044952 | 4/2012 |
| WO | WO 2012/169972 | 12/2012 |
| WO | WO 2014/138085 | 9/2014 |
| WO | WO 2015/109245 | 7/2015 |

OTHER PUBLICATIONS

Heidari et al (2019), Journal of Clinical Medicine, 8, 1439; doi:10.3390/jcm8091439.*
Balmert et al., "Positive Charge of 'Sticky' Peptides and Proteins Impedes Release from Negatively Charged PLGA Matrices," *J. Mater. Chem. B. Mater. Biol. Med.*, 3(23): 4723-4734, Jun. 21, 2015.
Buske et al., "Influence of PEG in PEG-PLGA microspheres on particle properties and protein release," *Eur. J. Pharm. Biopharm.*, vol. 81, pp. 57-63, Jan. 28, 2012.
Chang et al., "Biodegradable PLGA-Based Drug Delivery Systems for Modulating Ocular Surface Disease under Experimental Murine Dry Eye," *J. Clin. Exp. Ophthamol.*, 2(11): 13 pages, Nov. 1, 2011.
Derwent et al., "Thermoresponsive hydrogels as a new ocular drug delivery platform to the posterior segment of the eye," *Trans Am Ophthamol Soc*, 106: 206-214, 2008.

(Continued)

*Primary Examiner* — Prema M Mertz
(74) *Attorney, Agent, or Firm* — Klarquist Sparkman, LLP

(57) ABSTRACT

A method for treating an ocular disorder in a subject comprising administering a therapeutic agent-loaded carrier to an ocular site of the subject in need thereof, wherein the therapeutic agent loaded-carrier provides controlled delivery of the therapeutic agent under conditions suitable for recruiting regulatory T cells to an ocular region of interest or inducing regulatory T cells in an ocular region of interest.

10 Claims, 16 Drawing Sheets

(56) References Cited

OTHER PUBLICATIONS

Extended European Search Report issued by the European Patent Office for European Application No. 14761105.7 on Jul. 22, 2016.
Fedorchak et al., "Combating Blindness with Convenient and Comfortable Glaucoma Treatments," presentation delivered at McGowan Institute for Regenerative Medicine annual retreat Mar. 5, 2012.
Fedorchak et al., "28-day intraocular pressure reduction with a single dose of brimonidine tartrate-loaded microspheres," *Experimental Eye Research*, vol. 125, 210-216, Jun. 28, 2014.
Fedorchak et al., "28-Day Ocular Delivery of Brimonidine Tartrate from Rationally Designed Degradable Microparticles in a Rabbit Model," presentation delivered at Society for Biomaterials Oct. 4, 2012.
Fedorchak et al., "28-Day Ocular Delivery of Brimonidine Tartrate from Rationally Designed Degradable Microparticles in a Rabbit Model," presentation delivered at AIChE annual meeting Oct. 31, 2012.
Fedorchak et al., "Advanced Controlled Release Systems for Next Generation Ophthalmic Therapy," presentation delivered at Gordon Research Conference Mar. 22, 2012.
Fedorchak et al., "Combating Blindness with Convenient and Comfortable Glaucoma Treatments," presentation delivered at ARVO annual meeting May 4, 2012.
Final Office Action issued for U.S. Appl. No. 14/772,758 on Mar. 3, 2017.
Final Office Action issued for U.S. Appl. No. 14/772,758 on Jun. 14, 2018.
Gao et al., "A Microparticle/Hydrogel Combination Drug-Delivery System for Sustained Release of Retinoids," *Investigative Ophthamology & Visual Science*, 53:10, 6314-6323, Sep. 2012.
Glowacki et al., "Prevention of inflammation-mediated bone loss in murine and canine periodontal disease via recruitment of regulatory lymphocytes," *Proc. Natl. Acad. Sci. USA*, 110(46): 18525-18530, Nov. 12, 2013.
Ibrahim et al., "Novel Topical Ophthalmic Formulations for Management of Glaucoma," *Pharmaceutical Research*, 30(11): 2818-2831, Nov. 15, 2013.
International Application No. PCT/US2017/023455 filed Mar. 21, 2017.
International Search Report and Written Opinion issued in PCT/US2014/020355 mailed Jul. 10, 2014, 5 pages.
Jhunjhunjawala et al., "Controlled release formulations of IL-2, TGF-β1 and rapamycin for the induction of regulatory T cells," *Journal of Controlled Release*, 159(1): 78-84, Apr. 10, 2012.
Non-Final Office Action issued for U.S. Appl. No. 14/772,758 on Aug. 10, 2016.
Non-Final Office Action issued for U.S. Appl. No. 14/772,758 on Aug. 23, 2017.
Pisani et al., "Tuning microcapsules surface morphology using blends of homo- and copolymers of PLGA and PLGA-EPG," *Soft Matter*, vol. 5, p. 3054, Jul. 8, 2009.
Samarawickrama et al., "Retinoic acid and the ocular surface," *Survey of Ophthamology*, vol. 60, pp. 183-195, Oct. 16, 2014.
Stern et al., "Dry Eye as a Mucosal Autoimmune Disease," *Int. Rev. Imm.*, vol. 32, pp. 19-41, Jan. 29, 2013.
U.S. Appl. No. 16/087,470, filed Sep. 21, 2018.
Yang et al., "Hybrid Dendrimer Hydrogel/PLGA Nanoparticle Platform Sustains Drug Delivery for One Week and Antiglaucoma Effects for Four Days Following One-Time Topical Administration," *ACS Nano*, 6(9): 7595-7606, Aug. 9, 2012.

* cited by examiner

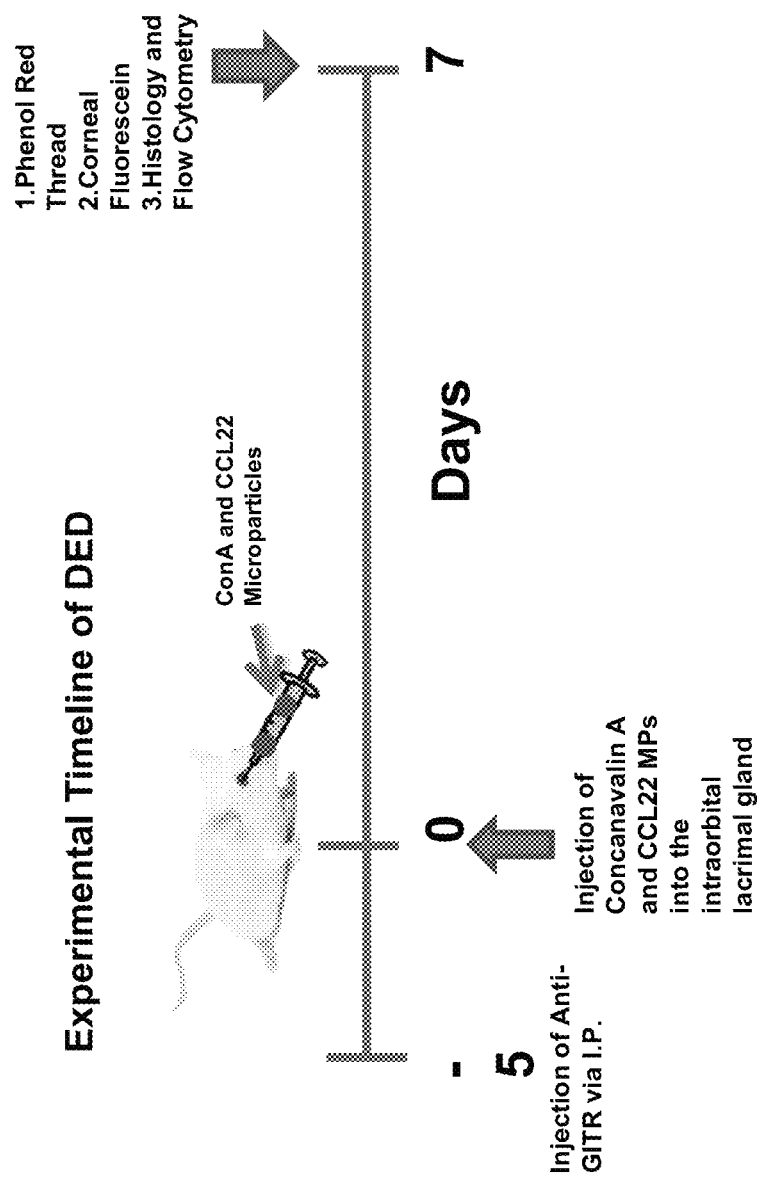

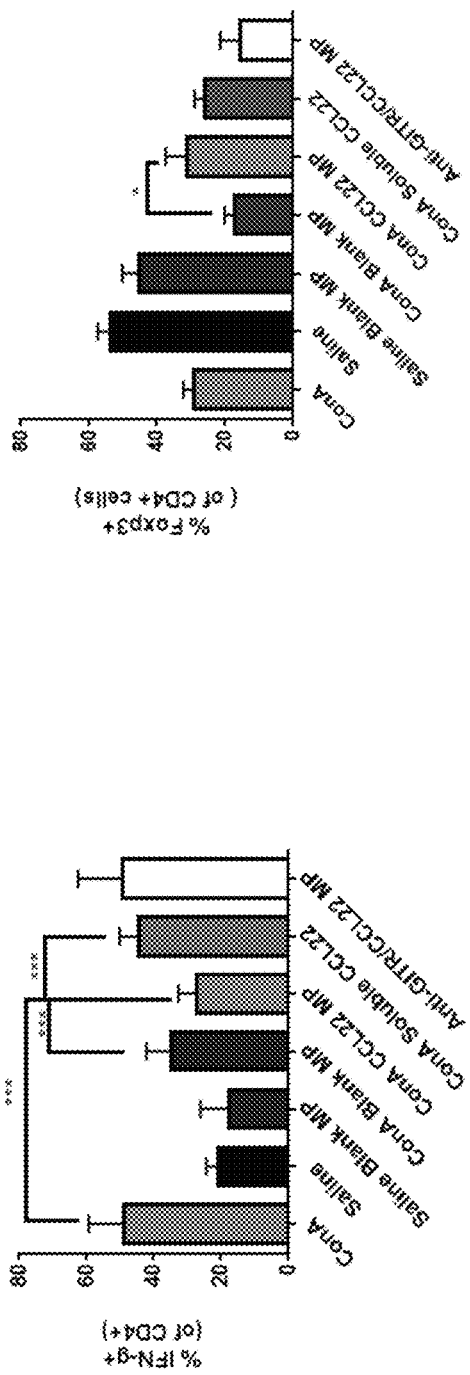
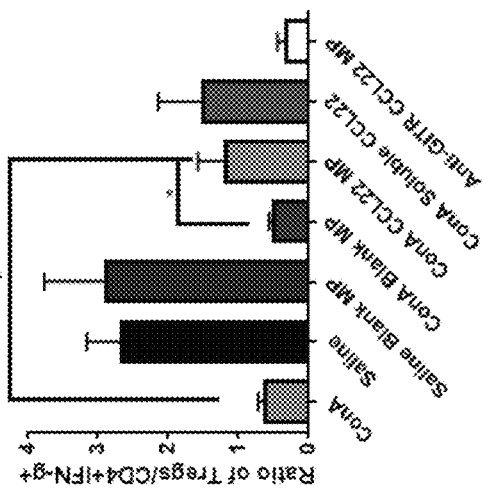
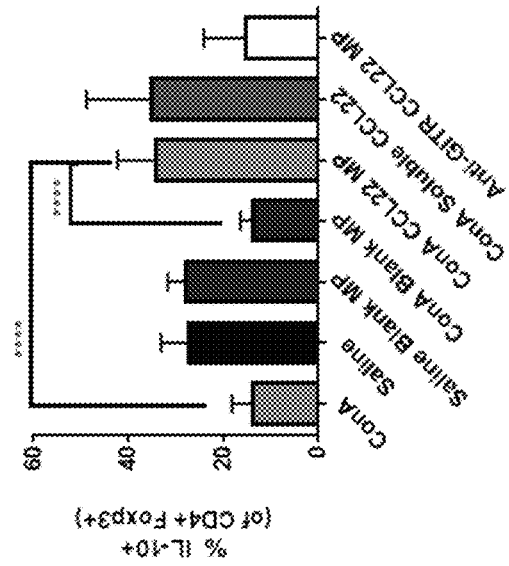
FIG. 5A  FIG. 5B  FIG. 5C  FIG. 5D

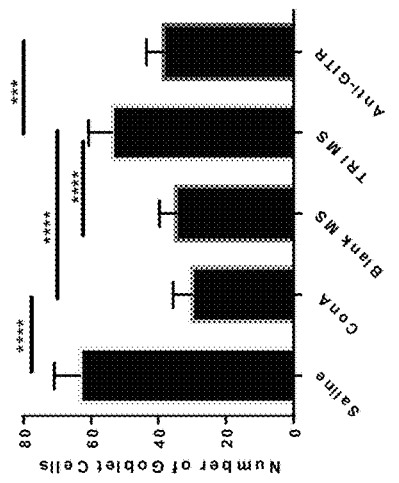
FIG. 10A
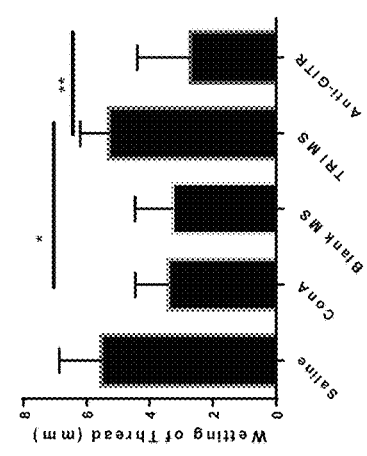
FIG. 10B
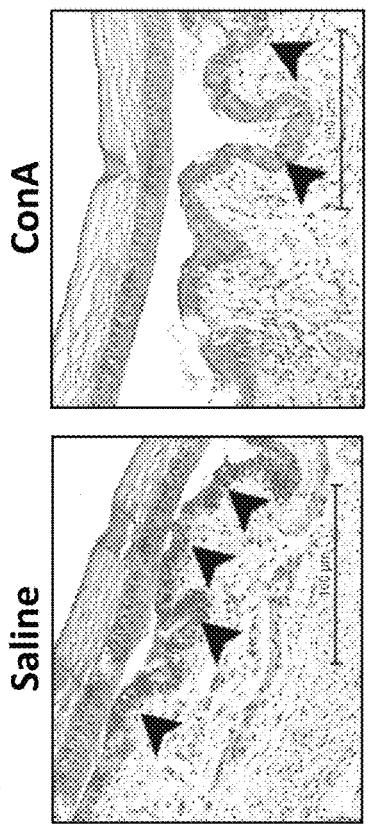
FIG. 10C
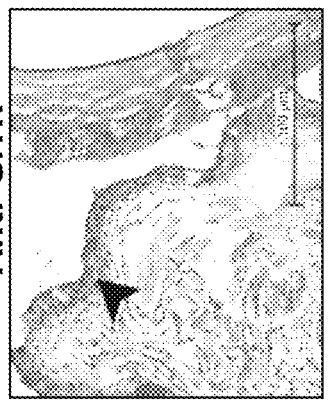
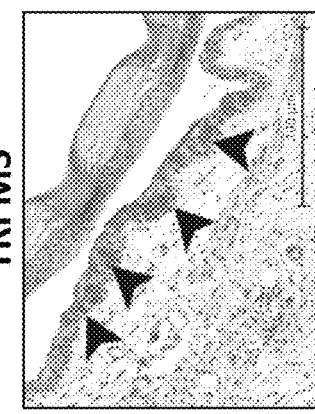
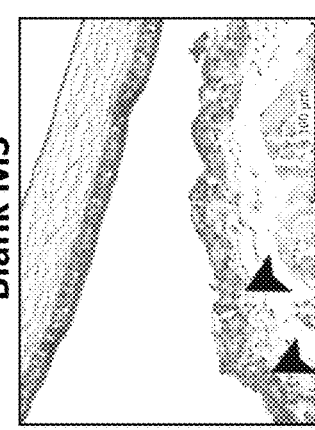

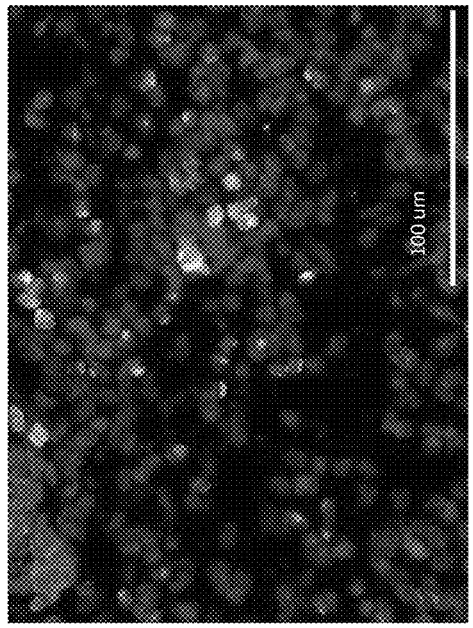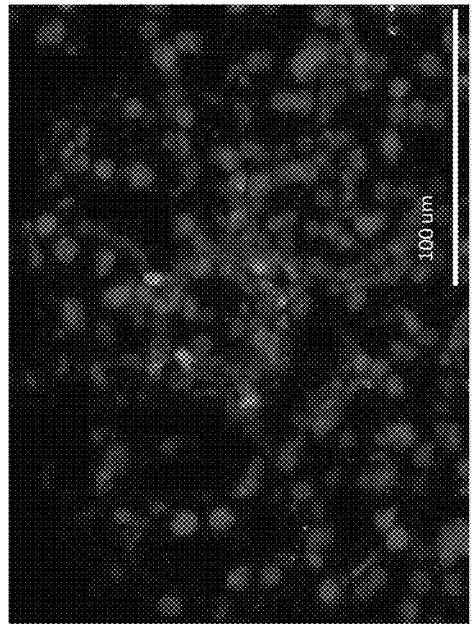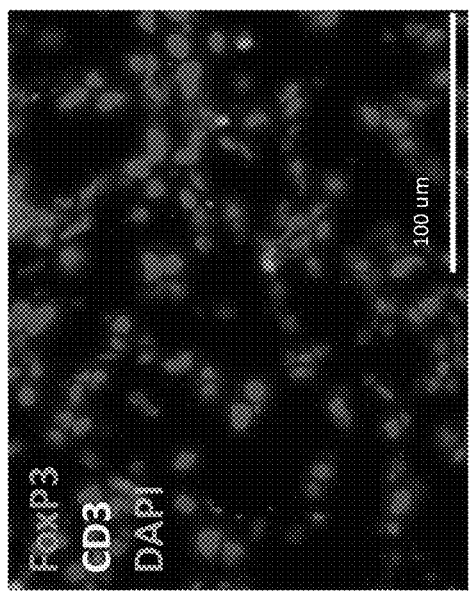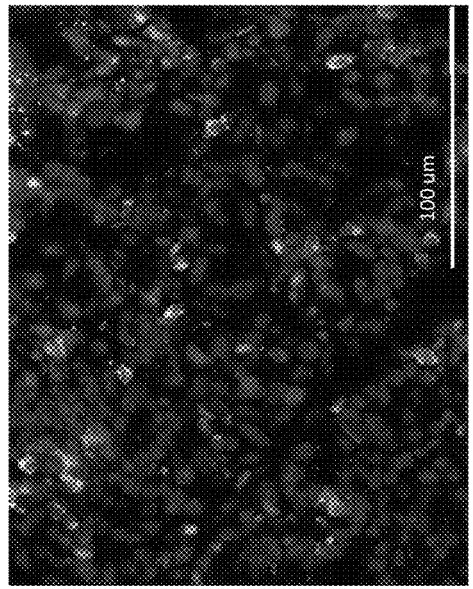
FIG. 13A
FIG. 13B
FIG. 13C
FIG. 13D

BIOMIMETIC DRUG DELIVERY OF AN IMMUNOMODULATORY AGENT FOR THE TREATMENT OF OCULAR CONDITIONS

CROSS REFERENCE TO RELATED APPLICATION

This application is a divisional of U.S. application Ser. No. 15/628,233, filed on Jun. 20, 2017, which claims priority to U.S. Application No. 62/353,908 filed on Jun. 23, 2016, which is incorporated herein by reference in its entirety.

BACKGROUND

To the best of our knowledge, current ophthalmic drug delivery systems do not provide a long term release of microparticles containing an immunomodulatory agent for the treatment of inflammatory eye diseases. The treatments for dry eye disease are based upon the condition. Mild treatments can include lifestyle changes, such as wearing sunglasses and less exposure to drying winds. Additional therapies to aid mild to moderate inflammation are tear substitutes. Artificial tears do provide temporary relief for patients; however, most formulations contain preservatives such as benzalkonium chloride that can cause eye irritation and hyperosmolarity of the tear film. Also, anti-inflammatory treatments are used for patients with severe inflammation. These treatments have shown to decrease inflammation in patients, however are only intended for short-term use, and long-term application has been implicated in conditions such as glaucoma and retinopathy. Other treatment approaches include, tear duct plugs, which reduce tear turnover. However, plugs do not address the underlying cause of the inflammatory disease.

Dry eye disease (DED) is a multifactorial ocular condition, characterized by inflammation of the ocular surface and tear film instability, which afflicts as many as 1 in 5 individuals globally. Individuals with DED suffer symptoms including blurred vision, foreign-body and/or burning sensation, light sensitivity, and in severe cases, corneal ulcerations leading to vision loss. Current treatments predominantly address the symptoms of DED and include artificial tears, punctual occlusion with tear plugs, and ophthalmic corticosteroids. Artificial tear substitutes may provide temporary relief for patients; however, most artificial tear formulations contain preservatives, such as benzalkonium chloride, which sometimes can cause tear film hyperosmolarity. This adverse effect can trigger death of mucin-producing goblet cells, leading to further ocular irritation. Tear plugs may be used with or without artificial tears to reduce tear turnover by occluding the draining tear duct; however, these punctal plugs must be inserted by a physician, and limitations include issues with plug retention and increased risk of ocular infections. Even with regular use of artificial tears and/or punctual plugs, many patients remain symptomatic because these palliative treatments do not address the underlying cause of DED. Recently, a number of studies demonstrated an inflammatory basis for DED, which led to the application of topical corticosteroids to treat DED. While ophthalmic corticosteroids broadly suppress ocular inflammation and can alleviate symptoms of DED, the effects are transient and are prescribed for short-term use. Consequently, treatment of DED typically requires long-term use of corticosteroids, which is associated with severe side effects, such as steroid-induced glaucoma and retinopathy. Furthermore, despite suppressing production of inflammatory mediators, corticosteroids do not address the underlying imbalance between pro-inflammatory immune cells and immunosuppressive cells.

In DED, infiltration of pathogenic pro-inflammatory $CD4^+$ T cells causes a breakdown in immunological homeostasis, ultimately compromising the lacrimal functional unit (LFU), which includes the cornea, conjunctiva, lacrimal glands, meibomian glands, and the interconnecting innervation. As T cells proliferate in the ocular tissues, these cells secrete pro-inflammatory cytokines, such as IFN-γ, which inhibit naturally suppressive immune cells known as regulatory T cells (Tregs). This ultimately leads to a shift in the immunological balance between tissue-protective Tregs and tissue-destructive pro-inflammatory (effector) T cells. Since the importance of Tregs contributing to immunological tolerance has become evident over the years, investigators have examined methods to utilize these immunosuppressive cells. Notably, adoptive transfer of Tregs from mice with DED can suppress inflammation in a T-cell deficient nude mouse administered effector T-cells from a DED mouse. Moreover, due to the low population of Tregs found in the human body (5-15%), application of ex vivo transfer of Tregs has been proposed as a method of therapeutic modulation in order to enhance the limited numbers of Tregs. Despite such evidence suggesting that enhancing Treg populations ex vivo is a viable therapeutic approach, there are many hurdles associated with translating a cellular-therapy to the clinic. These include expansion, contamination, and the potential hazard of Tregs differentiating into conventional T cells.

SUMMARY

Disclosed herein are methods for treating an ocular disorder in a subject comprising administering a therapeutic agent-loaded carrier to an ocular site of the subject in need thereof, wherein the therapeutic agent loaded-carrier provides controlled delivery of the therapeutic agent under conditions suitable for recruiting regulatory T cells to an ocular region of interest or inducing regulatory T cells in an ocular region of interest.

Further disclosed herein are methods for treating an ocular disorder in a subject comprising administering a therapeutic agent-loaded carrier to an ocular site of the subject in need thereof, wherein the therapeutic agent loaded-carrier provides controlled delivery of the therapeutic agent, the therapeutic agent is selected from CCL22, interleukin 2, rapamycin, transforming growth factor beta (TGF-β), retinoic acid, or vasoactive intestinal peptide (VIP), and the ocular disorder is dry eye disease, uveitis, allergic conjunctivitis, scleritis, or Age-Related Macular Degeneration (AMD).

Additionally disclosed herein are methods for treating an ocular disorder in a subject comprising administering a therapeutic agent-loaded carrier to an ocular site of the subject in need thereof, wherein the therapeutic agent loaded-carrier provides controlled delivery of the therapeutic agent under conditions suitable for activating regulatory T cells in an ocular region of interest.

Also disclosed herein is a composition comprising therapeutic agent-loaded microparticles, wherein the therapeutic agent is selected from CCL22, interleukin 2, rapamycin, transforming growth factor beta (TGF-β), retinoic acid, or vasoactive intestinal peptide (VIP), and the composition does not include a hydrogel.

The foregoing will become more apparent from the following detailed description, which proceeds with reference to the accompanying figures.

BRIEF DESCRIPTION OF THE DRAWINGS

FIG. 1 is a schematic timeline for CCL22 releasing PLGA microparticles for preventing Dry eye Disease (DED) in mice. Anti-GITR was injected via i.p. 5 days prior to administration of Concanavalin A and CCL22 MPs into the lacrimal gland.

(FIG. 2A) The treatment group of CCL2 MP does not significantly decrease tear production as compared to the experimental groups of ConA/Blank MP, which was significantly higher than ConA and equivalent to saline treatment (n=8) shown as mean±S.D. (FIG. 2B) The treatment group of CCL2 MP was able to maintain integrity of the epithelial layer of the cornea significantly than the ConA/Blank MP and ConA groups, and similar to the treatment group of saline alone, as observed by corneal fluorescein staining (FIG. 2C) A clinical score of the ocular surface staining, demonstrates that ConA/CCL22 MP treatment significantly decreases the permeability of the cornea as compared to ConA/Soluble CCL22, and ConA/Blank MP experimental groups (n=8) as shown as mean±S.D. * p≤0.05; p≤0.01; * p≤0.001

(FIG. 4A) Flow cytometry performed on the lymph nodes suggests the Saline MP treatment group has a significant percentage of infiltrating CD4+ lymphocytes in the cervical lymph nodes as compared to the diseased (ConA) (n=8) shown as mean±S.D. (FIG. 4B) CD4+ IFN-γ+ cells were analyzed to experimental groups (n=8) as shown as mean±S.D. (FIG. 4C) FoxP3+ Tregs was analyzed by flow cytometry in the lymph nodes (n=8) as shown as mean±S.D. (FIG. 4D) Foxp3− cells are significantly reduced in the cervical lymph nodes of the CCL22 MP group as compared to the ConA and ConA/Blank MP (n=8) as shown as mean±S.D. Significance was calculated using a One-Way Anova followed by Bonferroni post-hoc test * p≤0.05; p≤0.01; * p≤0.001

FIGS. 5A-5D: CCL22 MPs enhance anti-inflammatory responses in the lacrimal gland. (FIG. 5A) How cytometry performed on the lymph nodes suggests the CCL22 MP treatment group has a significant reduction of infiltrating CD4+ IFN-γ+ lymphocytes in the intraorbital lacrimal gland as compared to the diseased (ConA) and ConA/Blank MP (n=8) shown as mean±S.D. (FIG. 5B) Percentage of Tregs as determined by flow cytometry (n=8) as shown as mean±S.D. (FIG. 5C) Intracellular cytokine staining was determined after use of a cell stimulation cocktail to detect IL-10 expressing Tregs (FIG. 5D) The ratio of Tregs/T effectors was determined by CD4+ Foxp3+ to CD4+ IFN-γ+ cells. (n=8) shown as mean±S.D. Significance was calculated using a One-Way Anova followed by Bonferroni post-hoc test * p≤0.05;  p≤0.01; * p≤0.001

FIG. 6A) SEM of Porous blank microparticles (1000×). FIG. 6B) SEM of porous microparticles with CCL22 encapsulated (1000×). FIG. 6C) Coulter Counter: Average Volume Impedance measurements of Microparticles. FIG. 6D) Release Kinetics of porous CCL22 Microparticles

FIGS. 10A-10C. TRI MS prevent clinical signs of inflammation associated with DED (FIG. 10A) Wetting of phenol red threads were measured in millimeters using a dissecting microscope (n=6) shown as mean±S.D. (FIG. 10B) Representative images of histological sections of the eyes (20×) were quantified to identify differences in the Treg-inducing MS group compared to the diseased groups and non-diseased group (100 μm scale bar). (FIG. 10C) Goblet cells shown are the pink/purple (Periodic Acid Schiff stained) cells located in the conjunctiva labeled with arrows and the groups are shown as mean±S.D. * p≤0.05; p≤0.01; * p≤0.001, **** p≤0.0001.

(FIG. 11B) Clinical corneal fluorescein staining scores of the ocular surface on a scale of (0-4) (n=6) shown as mean±S.D. (n=6). * p≤0.05;** p≤0.01

FIG. 13A-13D. Representative lacrimal gland fixed frozen cryosections stained for T-cells (CD3$^+$ T cells—Cyan), Regulatory T-cells (FoxP3$^+$ T cells—Red), and nuclei (DAPI-blue). Scale bars are 100 μm FIGS. 14A-14I. Characterization of Treg-inducing Microspheres (FIG. 14A) Representative Scanning electron microscopy (SEM) image of Rapamycin microspheres (1000×) (FIG. 14B) Representative SEM image of IL-2 Microspheres (1000×) (FIG. 14C) Representative image of TGF-β1 Microspheres.

DETAILED DESCRIPTION

Terminology

Figure 2A:
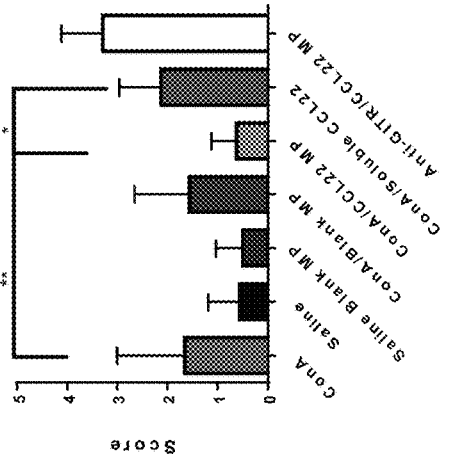
FIGS. 2A-2C: CCL22 microparticles prevent DED symptoms in mice.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of an agent disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the microparticles disclosed herein.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range; the term is used in reference to particles of sizes that can be, for example, administered to the eye in the form of an eye drop that can be delivered from a squeeze nozzle container, and thus can be less than 50 nm to 100 microns or greater. In certain embodiments, microparticles specifically refers to particles having a diameter from about 1 to about 25 microns, preferably from about 10 to about 25 microns, more preferably from about 10 to about 20 microns. In one embodiment, the particles have a diameter from about 1 to about 10 microns, preferably from about 1 to about 5 microns, more preferably from about 2 to about 5 microns. As used herein, the microparticle encompasses microspheres, microcapsules, microparticles, microrods, nanorods, nanoparticles, or nanospheres unless specified otherwise. A microparticle may be of composite construction and is not necessarily a pure substance; it may be spherical or any other shape.

"Ocular region" or "ocular site" means any area of the eye, including the anterior and posterior segment of the eye, and which generally includes, but is not limited to, any functional (e.g., for vision) or structural tissues found in the eyeball, or tissues or cellular layers that partly or completely line the interior or exterior of the eyeball. Ocular regions include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, the retina, and the lacrimal functional unit (LFU), which includes the cornea, conjunctiva, lacrimal glands, meibomian glands, and the interconnecting innervation.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat an ocular condition, or reduce or prevent ocular injury or damage without causing significant negative or adverse side effects to the eye or a region of the eye "Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as dry eye disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments, "treating" means reduction or resolution or prevention of an ocular condition, ocular injury or damage, or to promote healing of injured or damaged ocular tissue "Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, PA (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Disclosed herein are methods and compositions for treating ocular disorders. Illustrative disorders include, but are not limited to, dry eye disease, uveitis, allergic conjunctivitis, scleritis and Age-Related Macular Degeneration (AMD). In certain embodiments, the disorder is an inflammatory mediated ocular disorder, particularly in cases with chronic inflammation as an underlying cause.

The methods include administering a therapeutic agent-loaded carrier to a subject. The carrier may be in the form of a thin film, a rod, contact lens, or microparticles. In certain embodiments, the compositions include therapeutic agent-loaded microparticles.

Illustrative therapeutic agents include the natural, protein chemokine, C-C chemokine motif (CCL22), interleukin 2 (IL-2), rapamycin, transforming growth factor beta (TGF-β), retinoic acid, and vasoactive intestinal peptide (VIP).

In certain embodiments, the therapeutic agents are highly effective at recruiting Tregs, which is essential to the maintenance of immunological homeostasis to ensure the prevention of chronic inflammation and autoimmunity. In particular, CCL22, retinoic acid and VIP are effective at recruiting Tregs.

In certain embodiments, the therapeutic agents are highly effective at inducing Tregs, which is essential to the maintenance of immunological homeostasis to ensure the prevention of chronic inflammation and autoimmunity. In particular, IL-2, rapamycin and TGF-β are effective at inducing Tregs.

In certain embodiments, the therapeutic agent-loaded microparticles are highly effective at recruiting a specific type of T cell called a regulatory T-cell (Tregs), which is essential to the maintenance of immunological homeostasis to ensure the prevention of chronic inflammation and autoimmunity. The dissolvable microspheres are effective at recruiting endogenous Treg cells to a local site, naturally resolving inflammatory symptoms.

In certain embodiments, the method disclosed herein establish a therapeutic agent gradient to recruit Tregs to restore tissue damage in ocular disorders such as DED. For example, disclosed herein are Treg-recruiting CCL22 microparticles (CCL22 MPs) that when injected in the lacrimal gland increase the ratio of Tregs to $CD4^+$ $IFN-\gamma^+$ cells in the gland and reduce proliferation of $CD4^+$ lymphocytes in the regional draining lymph nodes suggesting that the reduction of effector T cells leads to the prevention of DED. Furthermore, CCL22 MPs prevent clinical signs of DED through the maintenance of aqueous tear production, preservation of goblet cell density, and corneal fluorescein staining. Thus, controlled release of CCL22 is able to recruit endogenous Tregs to restore tear film stability and ocular surface health.

Current topical therapeutics focus on providing agents acting as antagonists to hinder a specific cell involved in the pathogenesis of inflammatory eye diseases. However, long-term use of anti-inflammatory agents can cause retinopathy and glaucoma. The use of the microparticles disclosed herein is an approach to restore the homeostatic balance instead of solely targeting a pathogenic cell. Therefore, this treatment disclosed herein will resolve the underlying etiology of the disease, particularly dry eye disease. The methods and compositions disclosed herein also could result in a dramatic increase of patient compliance and reduce disease morbidity.

In one embodiment, disclosed herein are therapeutically-relevant, modular platforms to deliver therapeutic agents in vivo by artificial particles into the vicinity of Tregs. In one embodiment, the delivered agents modulate Treg cell proliferation. In one embodiment, the delivered factors modulate Treg cell immunosuppressive capacity.

In one embodiment, the method comprises introducing artificial microparticles in vivo wherein Tregs are recruited and/or activated. In one embodiment, the Treg cell recruitment and/or activation induces biological homeostasis thus resolving the ocular disease or condition.

In certain embodiments, the ocular disorder is treated via the induction of a subject's own Tregs from naïve $CD4^+$ T cells. This approach utilizes the body's own natural mechanism to differentiate peripheral naïve $CD4^+$ T cells into Tregs through a subset of antigen presenting cells known as tolerogenic dendritic cells (tDCs). Specifically, tDCs can induce differentiation of Tregs through the secretion of IL-2 and TGF-β cytokines. However, the maintenance of Tregs is somewhat more complex and depends on a local microenvironment that is not only favorable to differentiation of Tregs, but also unfavorable to differentiation into other effector T cells. One-way to ensure that cells do not differentiate into pathogenic effector T cells is through the small molecule, rapamycin. Rapamycin (Rapa) is an mTOR inhibitor that can suppress the generation and proliferation of effector T cells.

In certain embodiments, the body's own endogenous Tregs are enriched by delivering a combination of Treg inducing factors through TRI microspheres (TGF-β1, Rapamycin (Rapa), and IL-2). This local drug-delivery system is able to increase the prevalence of Tregs and, in turn, prevent key signs of dry eye disease such as aqueous tear secretion, conjunctival goblet cells, epithelial corneal integrity, and reduce the pro-inflammatory cytokine milieu in the tissue.

In certain embodiments, the amount of agent loaded into the microparticles may range from 1 ng to 1 mg, more particularly 1 to 100 μg, and most particularly, 20 to 30 μg agent per mg of microparticles. In certain specific embodiments, the amount of agent loaded into the microparticles is 25-30 μg agent per mg of microparticles.

The polymers for the microparticle may be bioerodible polymers so long as they are biocompatible. Preferred bio-erodible polymers are polyhydroxyacids such as poly-lactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpryrrolidone, alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

A preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, acid-terminated, referred to as 502H); poly(D,L-lactic-co-glycolic acid) (PLGA, 50:50 lactic acid to glycolic acid ratio, $M_n$=25 kDa, acid-terminated, referred to as 503H); poly(D,L-lactic-co-glycolic acid) (PLGA, 50:50 lactic acid to glycolic acid ratio, $M_n$=30 kDa, acid-terminated, referred to as 504H); poly(D,L-lactic-co-glycolic acid) (PLGA, 50:50 lactic acid to glycolic acid ratio, $M_n$=35 kDa, ester-terminated, referred to as 504); and poly(D,L-lactic-co-glycolic acid) (PLGA, 75:25 lactic acid to glycolic acid ratio, $M_n$=10 kDa, referred to as 752).

In certain embodiments, the polymer is an ester-terminated PLGA.

In certain embodiments, the polymer is a polyethylene glycol-poly(lactic-co-glycolic acid) copolymer.

In certain embodiments, the polymer microparticles are biodegradable.

In certain embodiments, the agent-loaded microparticles may have a volume average diameter of 200 nm to 30 µm, more particularly 1 to 10 µm. In certain embodiments, the agent-loaded microparticles do not have a volume average diameter of 10 µm or greater since such larger particles are difficult to eject from a container in the form of an eye drop. The agent-loaded microparticles may be pore less or they may contain varying amounts of pores of varying sizes, typically controlled by adding NaCl during the synthesis process.

In certain embodiments, the agent-loaded microparticle-containing composition does not include a hydrogel, particularly a thermoresponsive hydrogel.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics.

The microparticle disclosed herein may provide for sustained release of an agent. For example, the sustained release may be over a period of at least one day, more particularly at least 5 days or at least 10 days, and most particularly at least 30 days. The agent release can be linear or non-linear (single or multiple burst release). In certain embodiments, the agent may be released without a burst effect. For example, the sustained release may exhibit a substantially linear rate of release of the therapeutic agent in vivo over a period of at least one day, more particularly at least 5 days or at least 10 days, and most particularly at least 30 days. By substantially linear rate of release it is meant that the therapeutic agent is released at a rate that does not vary by more than about 20% over the desired period of time, more usually by not more than about 10%. It may be desirable to provide a relatively constant rate of release of the agent from the delivery system over the life of the system. For example, it may be desirable for the agent to be released in amounts from 0.1 to 100 µg per day, more particularly 1 to 10 µg per day, for the life of the system. However, the release rate may change to either increase or decrease depending on the formulation of the polymer microparticle. In certain embodiments, the delivery system may release an amount of the therapeutic agent that is effective in providing a concentration of the therapeutic agent in the eye in a range from 1 ng/ml to 200 µg/ml, more particularly 1 to 5 µg/ml. In certain embodiments, there is no initial lag phase of release. The desired release rate and target drug concentration can vary depending on the particular therapeutic agent chosen for the drug delivery system, the ocular condition being treated, and the subject's health.

The microparticle disclosed herein may provide for controlled release of an agent. The term "controlled release" as used herein, refers to the escape of any attached or encapsulated factor at a predetermined rate. For example, a controlled release of an agent may occur resulting from the predicable biodegradation of a polymer particle (i.e., for example, an artificial antigen presenting cell). The rate of biodegradation may be predetermined by altering the polymer composition and/or ratios comprising the particle. Consequently, the controlled release may be short term or the controlled release may be long term. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year.

In certain embodiments the agent-loaded microparticles may be included in a composition suitable for topical administration in the form of a liquid eye drop. The eye drop(s) may be administered to any ocular structure. The eye drops may be self-administered by the subject. The eye drop will conform comfortably to the conjunctival sac and release the loaded agent. The eye drop may be administered on a regimen wherein the interval between successive eye drops is greater than at least one day (although in certain embodiments the eye drop may be administered once daily or more than once daily). For example, there may be an interval of at least 5 days, at least one week, or at least one month between administrations of an eye drop(s). The agent-loaded microparticles disclosed herein drastically decreases the dosing frequency (thereby increasing the likelihood of patient compliance and recovery/prevention of worsening symptoms), it does so while avoiding clinician involvement for administration by being completely noninvasive.

The microparticle-containing composition disclosed herein may include an excipient component, such as effective amounts of buffering agents, and antioxidants to protect a drug (the therapeutic agent) from the effects of ionizing radiation during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In certain embodiments, the microparticles disclosed herein may be administered via injection. Injection sites include but are not limited to intraorbital lacrimal gland, extraorbital lacrimal gland, intraorbital injection, subconjunctival, intravitreal, posterior and anterior chambers of the eye.

Recent experimental and clinical investigations into the immunopathogenesis of DED suggest that the disorder is primarily mediated by $CD4^+$ T cells, which cause aberrant inflammation that contributes to ocular surface damage and tear film instability. More specifically, inflammation of the lacrimal gland leads to insufficient secretion of aqueous tear production resulting in clinical signs of DED. In order to mediate the development and perpetuation of inflammation, there is a sophisticated repertoire of CD4$^+$ T cells that maintain immunological tolerance and tissue homeostasis to ensure the prevention of chronic inflammation and autoimmunity. Specifically, this critical subset of T lymphocytes known as regulatory T cells (Tregs) are involved in stabilizing the immune microenvironment of the eye and actively regulating inflammation caused by an immune response mitigated via effector T cells.

The approach disclosed herein recruits endogenous Treg populations at the site of inflammation in order to promote an immunological balance between T effectors and Tregs ultimately preventing clinical signs of DED. In order to test the efficacy of the CCL22 MPs, an experimental murine dry eye disease model that induces inflammation using Concanavalin A (ConA), which nonspecifically expands and activates T cells through cross-linking the T cell receptor (FIG. 1), can be employed. Particularly, this murine model was selected, because DED has been thought to be primarily mediated by T cells.

Typically, inflammation associated with DED is characterized by symptoms of reduced tear film stability. We observed that administration of CCL22 MPs was able to effectively prevent the reduction in aqueous tear production seen in mice with ConA-induced DED (FIG. 2A). Notably, the protective/restorative effects on tear production required that CCL22 be sustainably released from MPs, as soluble CCL22 was unable to prevent loss of tear production (FIG. 2A). Studies suggest this could be due to the requirement of a chemokine concentration gradient to direct lymphocyte migration. While sustained release of CCL22 from degradable MPs can establish such a gradient for several days (e.g, at least two days) to weeks (e.g., at least two weeks), a bolus of CCL22 would quickly diffuse, forming a uniform concentration distribution. With the reduction of tear film ConA-induced DED mice, the lack of ocular surface lubrication leads to loss of corneal epithelial cells and the breakdown of intracellular tight junctions leading to an increase of corneal epithelial permeability. Ultimately, this allows fluorescein dye to diffuse into tissue spaces left by resident desquamated epithelial cells. Clinical implications corresponding to a decrease of corneal integrity can affect visual acuity. Interestingly, the CCL22 MPs were able to maintain ocular surface health, whereas ConA-induced DED mice (with or without Blank MPs) possessed statistically higher corneal fluorescein staining scores (FIGS. 2B and 2C), which traditionally is a clinical readout for corneal epitheliopathy. Together, the data suggest that CCL22 MPs are able to prevent clinical signs of DED induced inflammation directly correlating to disease severity.

Figure 3:
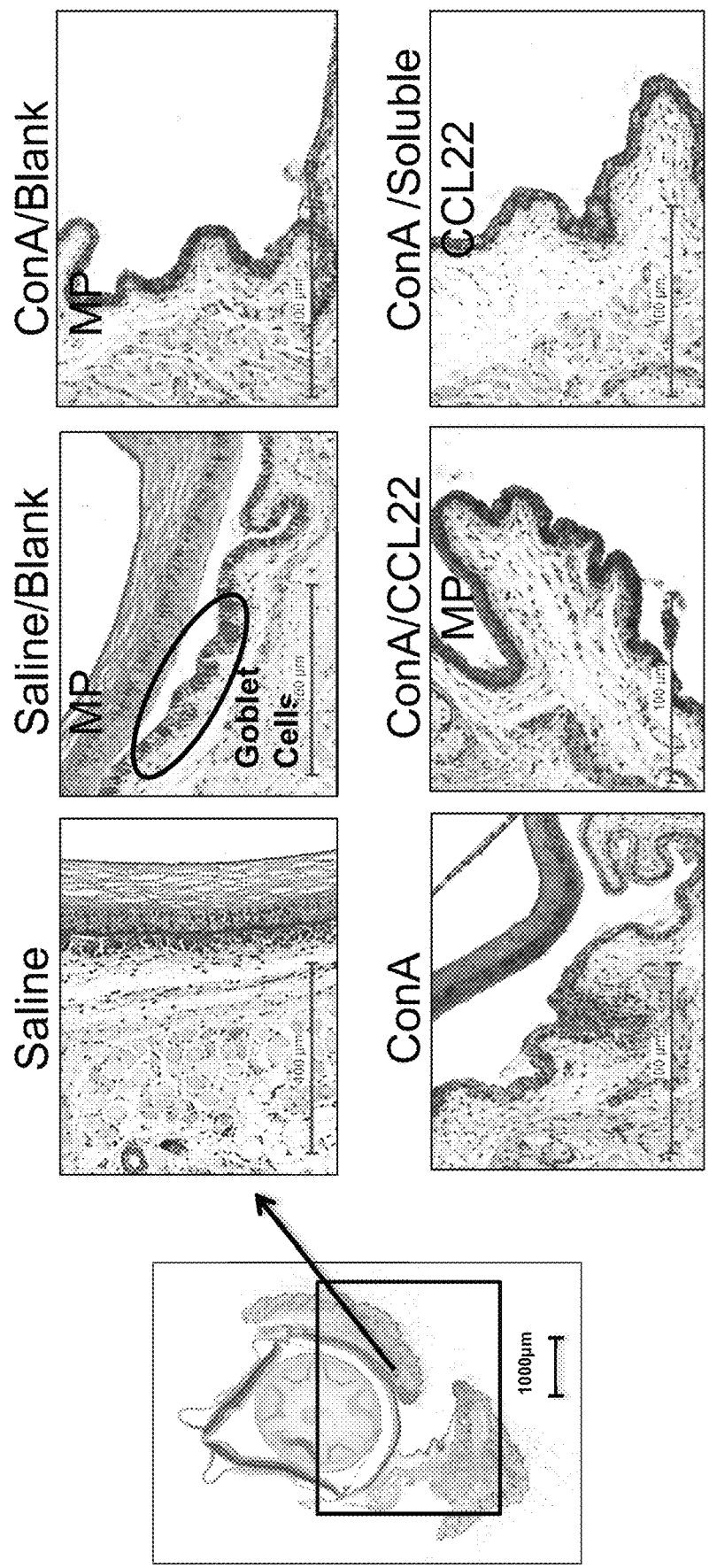
FIG. 3: CCL22 MPs prevent reduction of goblet cells in the conjunctiva. Representative histology images (20×) of PAS (Periodic Acid Schiff) murine conjunctiva. Significance was calculated using a One-Way Anova followed by Bonferroni post-hoc test * p≤0.05; p≤0.01; * p≤0.001

In DED, an increase of inflammation corresponds directly to conjunctival goblet cell apoptosis. To confirm that CCL22 MPs were maintaining goblet cell health, we analyzed histological sections of the conjunctiva in order to identify goblet cell density. Goblet cells secrete mucin, a component found in the tear film, which protect the ocular surface. As inflammation occurs to the ocular surface, the composition of the tear film is altered leading to a reduction of goblet cells and an increase of corneal fluorescein staining. We observed a decrease in the overall density of the mucin-filled goblet cells in mice with ConA-induced DED, relative to non-diseased (Saline) mice, which is consistent with corneal fluorescein images (FIG. 3). Loss of goblet cells might be due to higher levels of the Th1 cytokine (IFN-γ). Increased amounts of IFN-γ/IL-13 cytokines inhibit the promotion of goblet cell differentiation. More specifically, IFN-γ antagonizes production of IL-13, thus promoting apoptosis and squamous metaplasia of the goblet cells in the conjunctival epithelium. Notably, administration of CCL22 MPs maintained goblet cell density, as seen in the representative histological images compared to the diseased, diseased blank microparticles and soluble CCL22 (FIG. 3). Given that a loss of goblet cell density has shown to result from production of IFN-γ, we investigated lymphocyte populations in the regional draining lymph nodes and lacrimal gland, looking specifically at IFN-γ$^+$ T effectors and FoxP3$^+$ Tregs. We examined the lymph nodes, because this region serves as a reservoir for immune cells that can migrate to the ocular surface. Specifically, cervical lymph nodes, which drain from the eye, are critical sites for the induction of ocular surface inflammation through the activation of T effectors (FIG. 4). Moreover, these effector T cells migrate via chemokines such as CCR6 and CXCR3 from the cervical lymph nodes (CLN) to the ocular surface. Thus, we analyzed phenotypic expression of CD4$^+$ T lymphocytes in the regional draining superficial CLN. As expected with a T-cell mitogen, administration of ConA possessed significantly higher total CD4$^+$ T cell populations in the CLN. Furthermore, we identified increases of CD4$^+$ IFN-γ$^+$ Th1-type cells and activated T-effectors (CD4$^+$CD25$^+$FoxP3−) in the CLN of ConA-induced DED mice as compared to those treated with CCL22 MPs. This effect might be mediated due to the migration of dendritic cells to the regional lymph nodes via the chemokine CCR7, which activate pathogenic T cells that cause ocular surface and corneal inflammation. As immune cells migrate from the lymph nodes to the lacrimal gland, pro-inflammatory cytokines are secreted by the immune cells that perpetuate inflammation and negatively affect the function of the gland. Remarkably, as we examined the gland, data suggest the CCL22 MPs increased the amount of CD4$^+$ FoxP3$^+$ IL-10$^+$ Tregs in the lacrimal gland and ultimately shifted the ratio towards suppression resulting in a greater Treg/T effector balance compared to the diseased, and ConA+Blank MPs.

Figure 2B:
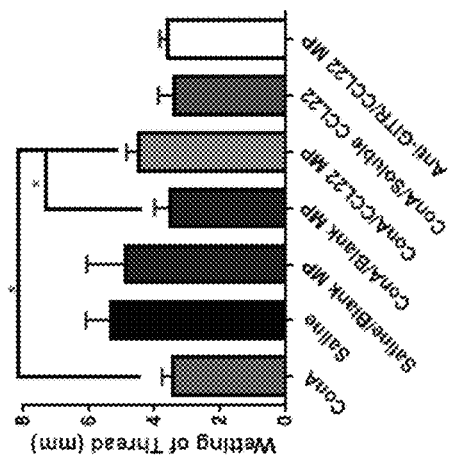
Figure 4A:
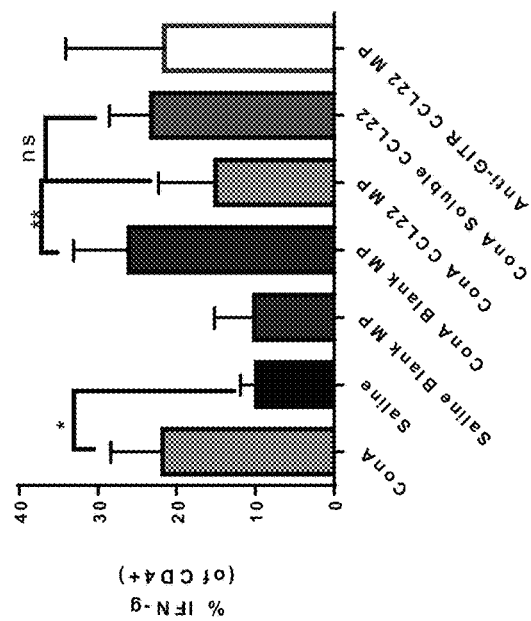
FIGS. 4A-4D: CCL22 Microparticles suppress T effector type of cells in the regional draining lymph nodes.
Figure 4B:
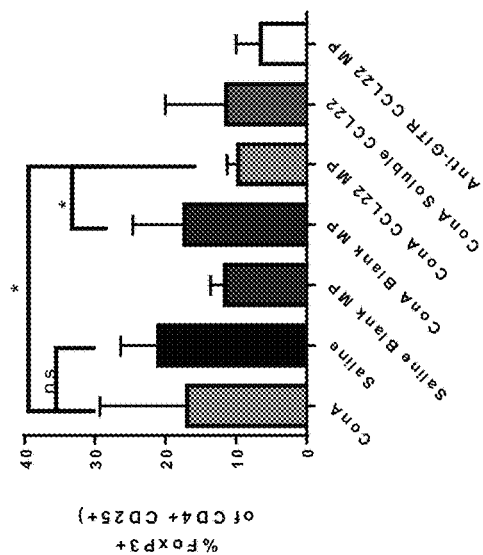
Figure 4C:
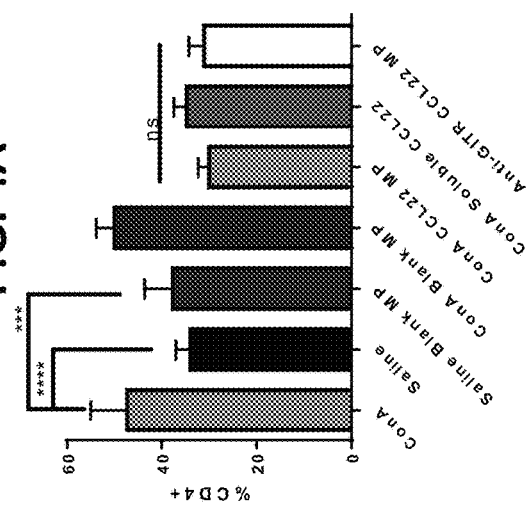
Figure 4D:
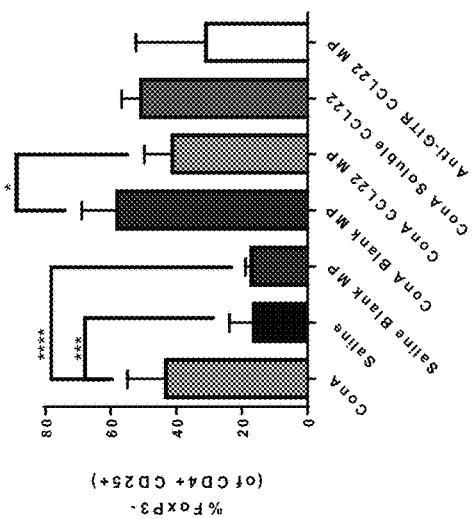
Figure 6C:
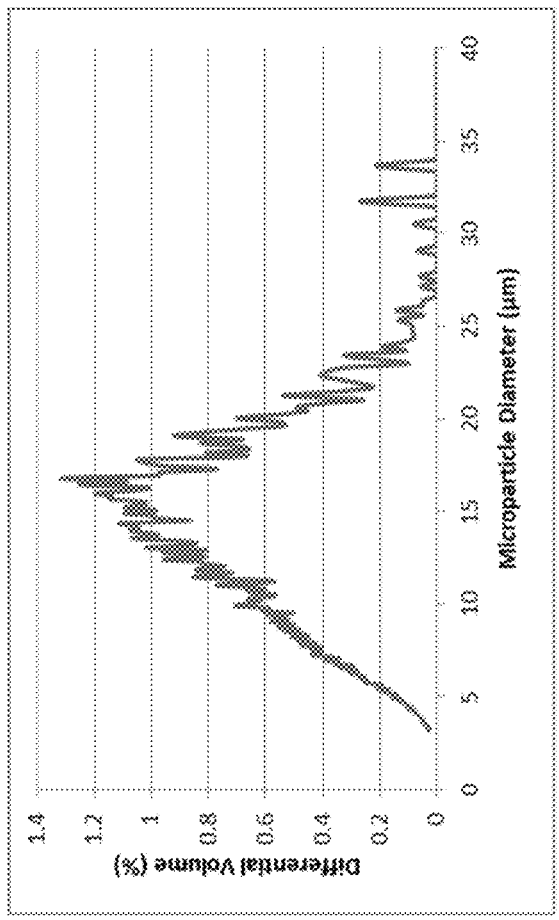
FIGS. 6A-6D: Characterization of engineered Porous microparticles loaded with the chemokine CCL22 and blank microparticles.
Figure 6D:
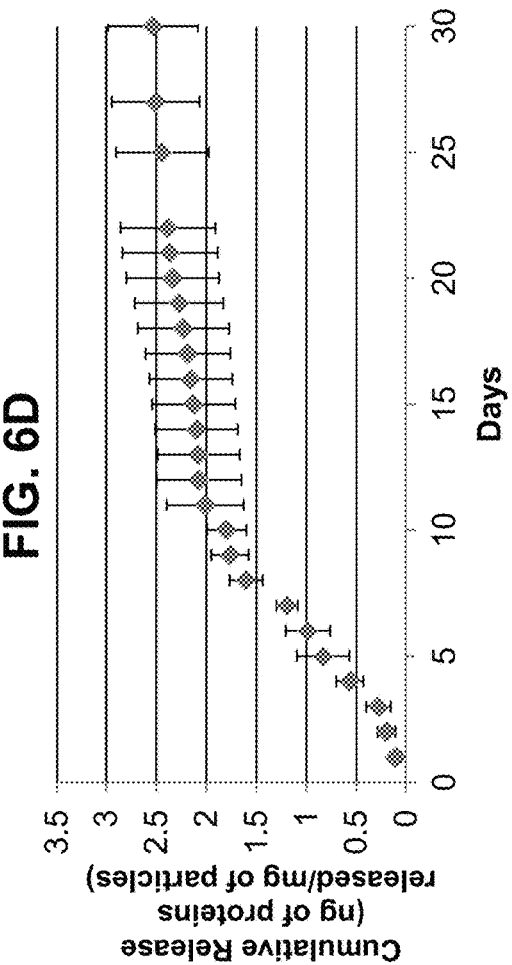
Figure 6A:
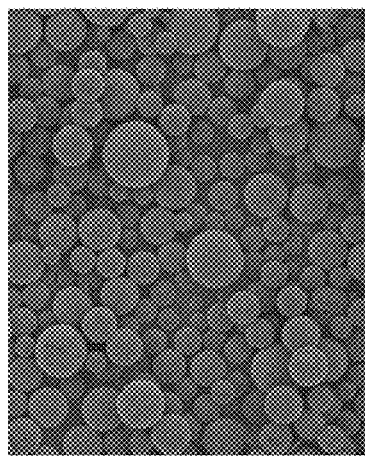
Figure 6B:
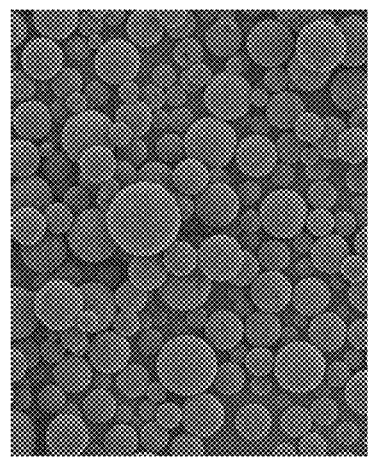

To demonstrate that CCL22 MP suppression of DED is mediated via Tregs, we used a GITR agonist (anti-DTA-1) to inhibit/block the suppressive effects of Tregs on other T cells. Anti-GITR modulates regulatory T cells through directly abrogating their suppressive function while co-stimulating other conventional T cells. The ability of anti-GITR to suppress Treg function and worsen clinical evaluations of DED is consistent with recent work that demonstrated the GITR ligand plays an integral role in ocular immunity regulating inflammation via the participation of photoreceptors. Additionally, administration of anti-GITR negated the therapeutic effects of CCL22 MP treatment, with reduced tear production (FIG. 2A) and increased corneal fluorescein staining (FIG. 2B, C). A significant influx of CD4$^+$ T cells occurred in the regional draining lymph nodes on anti-GITR compared to the all the groups (FIG. 4). In fact, this corresponded to an increase in the frequency of CD4$^+$ IFN-γ$^+$ Th1 cells and a decrease in the frequency of IL-10 producing Tregs in the lacrimal gland, compromising the immunological balance between T effectors and Tregs as compared to the administration of CCL22 MPs (FIG. 4C). Overall, anti-GITR reverses/neutralizes the effects of CCL22MPs, and in some cases yields greater pro-inflammatory cell populations than ConA alone.

Thus, we demonstrated that CCL22 MPs are capable of preventing inflammation in DED suggesting the potential broad applicability of this chemokine delivery system. Here we focused on an experimental murine model to prevent clinical signs of DED.

Several Illustrative Embodiments are Described Below in Following Numbered Clauses:

1. A method for treating an ocular disorder in a subject comprising administering a therapeutic agent-loaded carrier to an ocular site of the subject in need thereof, wherein the therapeutic agent loaded-carrier provides controlled delivery of the therapeutic agent under conditions suitable for recruiting regulatory T cells to an ocular region of interest.

2. The method of clause 1, wherein the regulatory T cells are endogenous.

3. The method of clause 1, wherein the ocular disorder is dry eye disease, uveitis, allergic conjunctivitis, scleritis, or Age-Related Macular Degeneration (AMD).

4. The method of clause 1, wherein the therapeutic agent is selected from CCL22, interleukin 2, rapamycin, transforming growth factor beta (TGF-β), retinoic acid, or vasoactive intestinal peptide (VIP).

5. The method of clause 1, wherein the ocular disorder is dry eye disease and the therapeutic agent is CCL22.

6. The method of clause 1, wherein the therapeutic agent-loaded carrier is in the form of therapeutic agent-loaded microparticles.

7. The method of clause 1, wherein the therapeutic agent-loaded carrier comprises therapeutic agent-loaded microparticles.

8. The method of clause 6, wherein the microparticles comprise poly (lactic-co-glycolic acid).

9. The method of clause 1, wherein the method provides controlled release under conditions to provide a concentration gradient within or near the ocular disorder site.

10. The method of clause 6, wherein the therapeutic agent-loaded microparticles are included in a composition that does not include a hydrogel.

11. The method of clause 5, wherein the therapeutic agent-loaded carrier is in the form of therapeutic agent-loaded microparticles.

12. The method of clause 11, wherein the microparticles comprise poly (lactic-co-glycolic acid).

13. A composition comprising therapeutic agent-loaded microparticles, wherein the therapeutic agent is selected from CCL22, interleukin 2, rapamycin, transforming growth factor beta (TGF-β), retinoic acid, or vasoactive intestinal peptide (VIP), and the composition does not include a hydrogel.

14. The composition of clause 13, wherein the microparticles comprise poly (lactic-co-glycolic acid).

EXAMPLES

Example 1—CCL22

Fabrication of Microparticles—Poly (lactic-co-glycolic) acid (PLGA) microparticles encapsulating recombinant mouse CCL22 (R&D Systems, Minneapolis MN) were made according to a previously reported water-oil-water double emulsion technique. Glowacki, A. J. et al. *Proc. Natl. Acad. Sci. U.S.A* 110, 18525-30 (2013). Briefly, 200 mg of RG502H poly(D,L-lactide-co-glycolide) polymer (Sigma Aldrich, St. Louis, MO) was dissolved in 4 ml of dichloromethane and vortexed. Then 2004, of an aqueous solution containing 5 μg of recombinant mouse CCL22 and 2 mg of BSA (Sigma Aldrich, St. Louis, MO) with 15 mmol NaCl was pipetted into the mixture of polymer and dichloromethane. Next, the first water-in-oil emulsion was prepared by sonicating the polymer and DCM solution with 150 μL of deionized water and 50 μL of CCL22 solution for a period of 10 seconds. Then the second water-oil emulsion was created by homogenizing (L4RT-A, Silverson) first water-oil emulsion with 60 mL 2% (wt./vol) polyvinyl alcohol (molecular weight ~25,000 g/mol, 98 mole % hydrolyzed; PolySciences) for a period of 60 seconds at 3,000 rpms. The homogenized solution was then mixed with 1% polyvinyl alcohol and placed onto a stir plate for 3 hours in order for the dichloromethane to evaporate. The microparticles were then collected and washed with deionized water in order to remove any remaining residual polyvinyl alcohol. Lastly, the microparticles were placed in 5 mL of deionized water, frozen in liquid nitrogen, and lyophilized for 72 hours (VirTis BenchTop K freeze dryer). The microparticles were stored at −20° C.

Characterization of Microparticles—Morphology of CCL22MPs was characterized using scanning electron microscopy (JEOL, JSM-6330F, Peabody, MA) and volume impedance measurements were completed on a Beckman Coulter Counter (Multisizer-3, Beckman Coulter, Fullerton, CA). In vitro release assays were completed by incubating 10 mg of CCL22 MPs in 1 ml of phosphate buffered saline (PBS), placed on a rotator at 37° C. Release media (supernatant) was sampled periodically and CCL22 concentrations were quantified using an enzyme-linked immunosorbent assay (ELISA) (R&D Systems, Minneapolis, MN). Mice—Six to eight-week-old female Balb/c mice. (Charles Rivers Laboratories, Wilmington, MA). The Institutional Animal Care and Use Committee approved the protocol, and all of the animals used in the experiments were treated according to the Association for Research in Vision and Ophthalmology Statement for the Use of Animals in Ophthalmic and *Vision Research*.

Experimental DED Model and Treatments—To induce DED, mice were anesthetized, and 200 μg of ConA (Sigma Aldrich, St. Louis, MO) in 20 μl of saline was injected into each intraorbital lacrimal gland (2 per mouse) with a 28.5 gauge needle using a dissecting microscope. DED treatments included Blank (empty) or CCL22 MPs (25 mg/ml), which were mixed with ConA or saline and injected. (Olympus SZX10, Waltham, MA). Soluble CCL22 was injected with ConA at 2.5 μg in 20 μl. To inhibit Treg function in vivo, anti-GITR (DTA-1) (BioXCell, Lebanon, NH) was injected i.p. (500 μg per mouse) five days prior to the injection of ConA and CCL22 MPs.

Measurement of Tear Production—Aqueous tear production was measured with phenol red cotton threads (Oasis Medical, San Dimas, CA). Thread was placed in the lateral canthus of the eye for a period of 60 seconds, and wetting was measured in millimeters using a dissecting microscope (Olympus SZX10, Waltham, MA).

Corneal Permeability—To evaluate the corneal epithelial layer, fluorescein stain (1 uL of 1% solution) was applied to the conjunctival sac and 5 μl of saline was used to wash off any excess dye. The surface of the cornea was evaluated using a dissecting microscope with a fluorescent excitation lamp (Olympus SZX10, Waltham, MA). Eyes were evaluated in a masked fashion by an independent ophthalmologist, and scored 0 for no staining, score 1 for a quarter of staining, score of 2 for less than a half, score of 3 for half, and 4 for more than half of the eye. Histopathology—At the end of the study, eyeballs were exenterated then harvested and fixed in formalin for 24 hours. Eyes were sectioned 5 μm thick and stained with Periodic Acid Schiff (PAS) to identify goblet cells in the conjunctiva. The histology section images were scanned using a Zeiss Axio Scan. Z1 (Thornwood, NY).

Immunophenotype Analysis by Flow Cytometry—Lacrimal glands and draining cervical lymph nodes were harvested from the experimental murine groups at the end of the study, and single cell suspensions were prepared. Cells were stained with the following fluorescent conjugated antibodies: anti-CD4 eFluor450 (RM4-5), anti-CD25 APC-Cy7 (PC61), anti-FoxP3 PE (FJK-16s) (eBioscience, San Diego, CA and BD Bioscience, San Jose, CA). For intracellular cytokine staining, the cells were placed in a 96-well plate overnight in cell culture media with Cell Stimulation Cocktail (plus protein transport inhibitor) for a period of 12 hours and stained with anti-IL-10 APC (JES5-16E3), and anti-IFN-γ FITC (XMG 1.2) (eBioscience, San Diego, CA). Stained cells were analyzed with BD FACSDiva software, v6.1.3.

Statistical Analysis—Data expressed as mean±S.D. Comparisons between multiple treatment groups were performed using one-way ANOVA, followed by Bonferroni multiple comparisons, and p<0.05 was considered statistically significant. Statistical tests were performed using GraphPad Prism Software 6.0 (GraphPad Prism, San Diego, CA)

Results

CCL22 MPs Prevent Clinical Symptoms of DED.

Figure 2C:
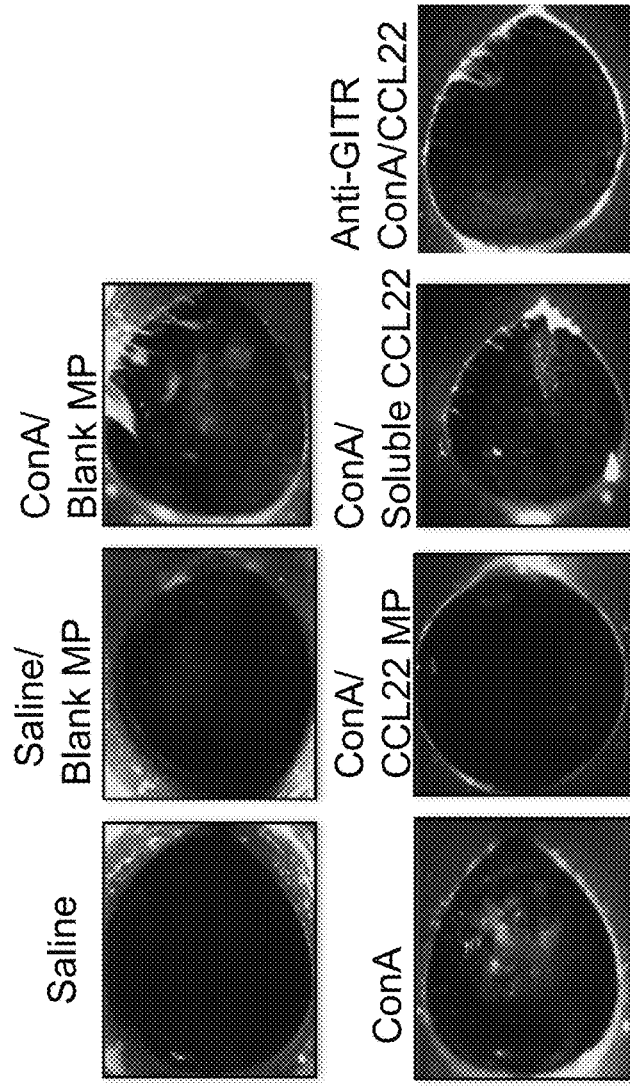

To assess whether CCL22 MPs could prevent clinical evaluations associated with DED, several aspects such as tear production, corneal fluorescein staining, and goblet cell density were examined One week after inducing DED, we hypothesized that ConA, the DED-inducing agent, would decrease tear production, while ConA plus treatment with CCL22 MPs would prevent a decrease of tear production. As expected, ConA significantly reduced tear secretion, relative to control mice (Saline injection). Meanwhile, the effect of incorporating the CCL22 MPs with either ConA or Saline was examined to determine if the chemokine microparticles were able to prevent a decrease in tear volume. CCL22 MPs and Blank (unloaded) MPs were injected (0.5 mg MPs/20 µl) with ConA to determine if CCL22 MPs were able to prevent the clinical symptoms associated with DED. The ConA+ CCL22 MP group prevented tear production loss to levels comparable to non-diseased (saline) mice, while treatment with ConA and ConA+ Blank MP significantly reduced tear production similarly (FIG. 2A) Additionally, we wanted to confirm that injecting microparticles does not contribute to symptoms associated with DED. Therefore, we examined the effects of blank microparticles in saline to identify if they had an effect on tear secretion. As shown in FIG. 2A, the Saline Blank MPs possessed no significant difference in tear secretion relative to the saline group at the conclusion of the study. CCL22 MP administration also appears to maintain the integrity of the corneal epithelium. Corneal permeability, which is decreased with a faster rate of fluorescein elimination in healthy patients as compared to those with DED, was visually evaluated by comparing uptake of fluorescein staining on the corneal epithelium. Consistent with an intact/undamaged cornea, no staining was observed on the corneas of control mice (Saline and Saline Blank MP) after instillation of fluorescein. In contrast, central punctate fluorescein staining was observed on corneas of the ConA, ConA+Blank MP, and ConA+Soluble CCL22 groups (FIG. 2B). The fluorescein dye also appeared to stain the tear film in these groups. However, mice treated with ConA+CCL22 MPs showed no significant increase in corneal staining relative to non-diseased (Saline control) mice (FIG. 2C).

After one week, eyes were exenterated, and the conjunctiva was Periodic Acid Schiff (PAS) stained to identify goblet cells interspersed throughout the stratified squamous cells of the conjunctiva. Goblet cells play an important role in lubrication of the eye through the production of mucin, which is a component of the tear film. As a loss of goblet cell density occurs, tear film composition changes correlating to severity of conjunctival disease. Treatment with ConA or ConA+ Blank MP led to a decrease in goblet cell density compared to the non-diseased (Saline or Saline+ Blank MP) control groups (FIG. 3). Notably, treatment of DED (ConA) mice with CCL22 MPs restored goblet cell density to levels seen in non-diseased mice (FIG. 3).

CCL22 MPs Suppress Proliferation of $CD4^+$ T Cells in Regional Draining Lymph Nodes.

Figure 7:
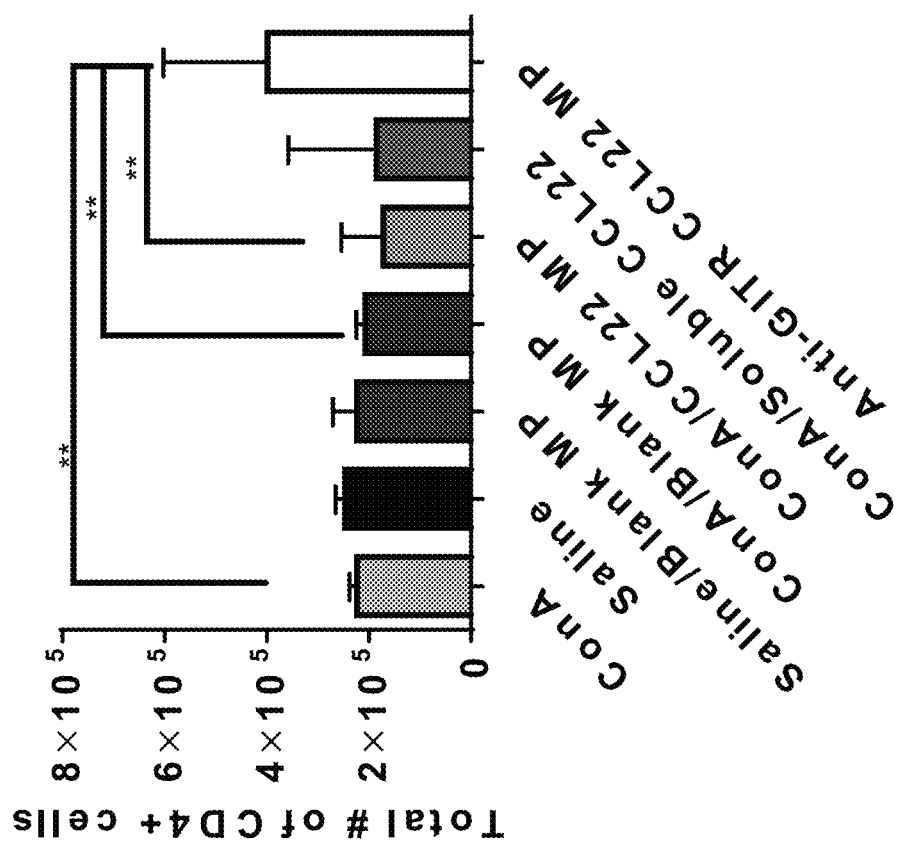
FIG. 7: Flow Cytometry of Inguinal Lymph Nodes. Total CD4+ cells in the inguinal lymph nodes show a significant difference in the Anti-GITR CCL22 MP group as compared to ConA/CCL22 MP
Figure 8:
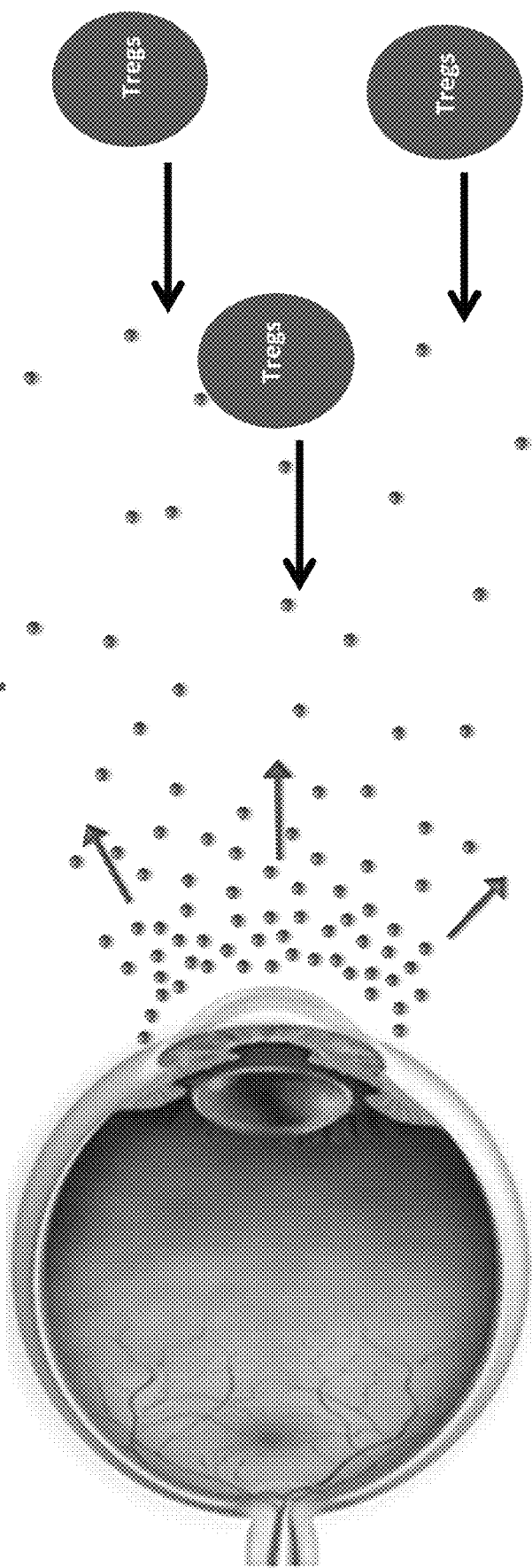
FIG. 8 is a representation of the application of CCL22 microparticles to recruit functional regulatory T cells to the eye.

Previous investigations into DED have demonstrated ocular inflammation is mediated primarily by CD4+ T cells. Moreover, studies have identified an increased proliferation of T cells in the draining lymph nodes of mice with DED. Additionally, it has been shown that CCL22 MPs can attract Tregs and skew T-cell populations locally. Glowacki, A. J. et al. *Proc. Natl. Acad. Sci. U.S.A* 110, 18525-30 (2013). Thus, to determine whether CCL22 MP-mediated suppression of DED symptoms was due to effects on the activation of T cells in the regional lymphoid tissue, we performed a phenotypic analysis of T-cell populations in the cervical lymph nodes (CLN). Total cells counts were included due to the significant increase in overall cell counts with the administration of ConA. CLN from mice with DED induced by ConA (with or without Blank MPs) exhibited significantly greater total numbers of CD4+ T cells (FIG. 3A). To further confirm the T-cell mediated immune response, we examined the expression of the intracellular cytokine, IFN-γ. Results suggest that CCL22 microparticles possess a decrease of $CD4^+IFN-\gamma^+$ cells (FIG. 3B). However, the diseased mice had significantly higher levels of $CD4^+IFN-\gamma^+$ (Th1) T cells (FIG. 3B), $CD4^+CD25^+FoxP3^+$Tregs (FIG. 3C), and $CD4^+CD25^+$Foxp3– (Activated T-effectors) (FIG. 3D), than CLN from CCL22 MPs and the non-diseased (Saline or Saline+Blank MP) control mice. Notably, CCL22 MP administration significantly reduced total numbers of activated T-effectors as compared to the diseased mice (FIG. 3D). Interestingly, there was a decrease in the total amount of Tregs. However, the decrease in Tregs was not as dramatic as the decrease of $IFN-\gamma^+$ cells for the CCL22 MP as compared to the diseased, ConA+ Blank MP, and ConA+ Soluble CCL22 (FIG. 3C). Finally, to confirm that there were no systemic effects of ConA and/or CCL22MPs, we harvested distal inguinal lymph nodes, and performed a similar phenotypic analysis of $CD4^+$ T cells and $CD4^+$ $CD25^+FoxP3^+$ T cells (FIG. 7). We did observe a significant difference in $CD4^+$ lymphocyte count in the inguinal lymph nodes among any experimental groups, suggesting there is a systemic affect due to the Anti-GITR. Results suggest that the CCL22 MPs have a significantly lower population of IFN-γ producing T cells in the CLN relative to the diseased control groups.

CCL22 MPs Reduce Infiltration of $CD4^+$ $IFN-\gamma^+$ T cells in the Lacrimal Gland.

In DED, inflammation of the lacrimal gland increases the production of pro-inflammatory cytokines, which results in lymphocyte homing and proliferation. Ultimately, the infiltration of lymphocytes and secretion of pro-inflammatory cytokines inhibit the normal function of the gland. To determine whether CCL22 MPs alter T-cell populations in the lacrimal gland, we harvested the intraorbital lacrimal glands and used flow cytometry to analyze T-cell populations in this tissue. Specifically, we looked at frequencies of pro-inflammatory $CD4^+$ $IFN-\gamma^+$ (Th1) T cells and $CD4^+$ $FoxP3^+$ Tregs in the gland. Lacrimal glands from mice with DED induced by ConA (w/or w/o Blank MP) had significantly greater proportions of $IFN-\gamma^+$ T cells (FIG. 5A) and significantly lower proportions of FoxP3+ Tregs (FIG. 5B), relative to non-diseased (saline w/or w/o Blank MP) mice. Notably, DED mice treated with ConA+CCL22 MPs showed a significant reduction in the frequency of IFN-$\gamma^+$ cells with a concomitant increase in the frequency of FoxP3$^+$ Tregs (FIG. 5A,B), relative to ConA alone. A large proportion of the FoxP3$^+$ Tregs also expressed the suppressive cytokine IL-10 (FIG. 5C). Ultimately, the shifts in pro-inflammatory cytokine, IFN-$\gamma^+$ and anti-inflammatory Treg populations with CCL22 MPs contributed to a two-fold increase in the Treg/Th1-type ratio, relative to ConA alone (FIG. 5D) while the Treg/Th1-type ratio for the ConA+CCL22 MP group was still significantly less than that for non-diseased (Saline or Saline+ Blank MP) mice. In addition, we identified that there was a significant increase in the total amount of CD4$^+$ T cells in the diseased mice and fewer total cells in the CCL22 MP group. Specifically, CD4$^+$IFN-$\gamma^+$ total cells were lower in the CCL22 MP administered group. Collectively, the data suggest there is a significant reduction of T lymphocytes in the regional draining lymph nodes compared to the negative controls.

Administration of Anti-GITR Disables Regulatory T Cell Function.

To explore deeper the role of CCL22 MP recruitment of endogenous Tregs to reduce inflammation in the DED model, we wanted to confirm that the suppressive effects suggested by our data were due to Tregs. A glucocorticoid-induced tumor necrosis factor receptor (GITR) agonistic antibody (Anti-GITR) was administered 5 days before injection of ConA and CCL22 MPs (FIG. 1A). The outcome of anti-GITR essentially inhibits the ability of Tregs to suppress other T cells (non-Tregs). Importantly, anti-GITR injected before treatment with ConA and CCL22 MPs appeared to abrogate the symptom-reducing effects of CCL22 MPs, with aqueous tear production and punctate staining of the cornea comparable to (or worse than) that of mice treated with ConA alone (FIG. 2A,B). Additionally, mice treated with anti-GITR before ConA+CCL22 MPs had significantly greater numbers of total CD4$^+$ T cells and activated T effectors, and comparable numbers of IFN-$\gamma^+$ Th1-type cells in the CLN, relative to mice treated with ConA alone (FIG. 4). Moreover, the lacrimal gland tissue of mice treated with anti-GITR, ConA, and CCL22MP had similar frequencies of CD4$^+$ IFN-$\gamma^+$ T cells, FoxP3$^+$ Tregs, and IL-10$^+$ producing Tregs as mice with ConA-induced DED (FIG. 5). Taken together, these results indicate that using anti-GITR to inhibit Treg-mediated suppression reverses the therapeutic effects of CCL22 MPs in the DED model at the symptom and underlying immunological levels.

Example 2—TRI Microspheres

Fabrication of Microspheres—TGF-$\beta$1 and IL-2 microspheres were fabricated using a double emulsion-evaporation technique. For the TGF-$\beta$1 microspheres, Poly (lactic-co-glycolic) acid (PLGA-50:50 lactide:glycolide, acid terminated) (MW:7,000-17,000) (viscosity: 0.16-0.24 dL/g, 0.1% (w/v) in chloroform) (Sigma Aldrich, MO) and PEG-PLGA (PolySciTech, IN) was used to encapsulate rh-TGF-$\beta$1 (PeproTech, NJ). Specifically, 170 mg of PLGA and 30 mg of PEG-PLGA was dissolved in 4 ml of DCM (Sigma Aldrich, MO). Then 200 µl of aqueous solution containing 10 µg of rh-TGF-$\beta$1 was added to the polymer DCM mixture. The mixture was sonicated using a sonicator (Vibra-Cell, Newton, CT) for 10 sec. at 25% amplitude. Next, this emulsion was then mixed with 60 ml of 2% polyvinyl-alcohol (PVA, MW ~25,000, 98% hydrolyzed; PolySciences) and homogenized (L4RT-A, Silverson, procured through Fisher Scientific) at 3,000 rpm for 1 min. The homogenized mixtures were then added to 80 ml of 1% PVA on stir plate and left for 3 hours in order for the DCM to evaporate. After 3 hours, the microparticles were centrifuged (200 g, 5 min, 4° C.), washed 5 times with deionized water, and lyophilized for 48 hours (Virtis Benchtop K freeze dryer, Gardiner, NY).

For the IL-2 microspheres, 200 mg of PLGA (PLGA-50:50 lactide:glycolide, acid terminated) (MW:7,000-17,000) (viscosity: 0.16-0.24 dL/g, 0.1% (w/v) in chloroform) (Sigma, Aldrich, MI) was combined with 4 ml of DCM. Subsequently, 5 µg of IL-2 and 150 µl (R&D Systems, Minneapolis MN) of deionized water was added to the polymer dissolved in DCM. Next, the mixture was emulsified using a sonicator probe (Vibra-Cell, Newton, CT) at 25% amplitude for a period of 25 seconds. Then this emulsion was mixed with 60 ml of 2% polyvinyl-alcohol (PVA, MW ~25,000, 98% hydrolyzed; Polysciences) and homogenized (L4RT-A, Silverson, procured through Fisher Scientific) at 3,000 rpm for 1 min. This secondary emulsion was then then added to 80 ml of 1% PVA on stir plate and stirred for 3 hours. After finishing stirring, the microparticles were centrifuged (200 g, 5 min, 4° C.), washed 5 times with deionized water, and lyophilized for 48 hours (Virtis Benchtop K freeze dryer, Gardiner, NY).

Lastly, the rapamycin (rapa) microspheres were fabricated using a single emulsion-evaporation technique due to the hydrophobic nature. Rapamycin (Sigma Aldrich, MO) was dissolved in DMSO (Sigma, Aldrich, MO) at 10 mg/ml. Then 200 mg of PLGA (Sigma Aldrich, MI) was dissolved in 4 ml of DCM. Next, 100 µl of rapamycin (10 mg/ml) was added to the polymer/DCM mixture. The solution was then homogenized with 60 ml of 2% PVA at 3,000 rpm for 1 min. After homogenizing, the emulsion was then added to 80 ml of 1% PVA and stirred for 3 hours. At the end of stirring, the microspheres were washed 5 times with deionized water and lyophilized for 48 hours.

Characterization of Microspheres—The morphology of the microspheres were characterized using scanning electron microscopy (JEOL, JSM-6330F, Peabody, MA) and volume impedance measurements were performed on a Beckman Coulter Counter (Multisizer-3, Beckman Coulter, Fullerton, CA). The release assay of the IL-2, TGF-$\beta$1, and rapamycin was completed by incubating 10 mg of microspheres in 1 ml of phosphate buffered saline (PBS) and 1% BSA, which was placed onto a rotator at 37° C. The supernant was sampled at different time intervals and the TGF-$\beta$1 and IL-2 release profiles were quantified using an enzyme-linked immunosorbent assay (ELISA) (R&D Systems, Minneapolis, MN). The release profile of the rapamycin microspheres were characterized using UV-vis spectroscopy and the release media contained 0.2% Tween-80 in PBS (absorbance at 278 nm).

Mice—Female Balb/c mice aged 6-8 weeks were used in this experimental study. (Charles Rivers Laboratories, Wilmington, MA). The Institutional Animal Care and Use Committee, University of Pittsburgh approved all murine experiments.

Murine DED model and treatment—Dry eye disease was induced using 10 mg/ml of Concanavalin A (ConA) (Sigma Aldrich, St. Louis, MO) in phosphate buffered saline solution (PBS) was injected (30 µl) into the lacrimal glands with a 28.5 gauge needle using a dissecting microscope. The controls for examining the effects of the TRI MS included Blank (unloaded) or TRI MS (25 mg/ml), which were combined with a PBS solution of ConA (10 mg/ml). (Olympus SZX10, Waltham, MA).

Suppression of Tregs Via the Administration of Anti-GITR

In order to identify the role of Tregs with the administration of our preventative treatment, the function of Tregs were inhibited using anti-GITR (DTA-1) (BioXCell, Lebanon, NH) via an intraparietal injection of (500 μg per mouse) 1 day after injecting the ConA and TRI MS.

Tear Production—Phenol red cotton threads were utilized to measure tear production. (Oasis Medical, San Dimas, CA). The thread was placed in the lateral canthus of the eye for a period of 60 seconds, and the amount of wetting on the thread was measured using a dissecting microscope (Olympus SZX10, Waltham, MA).

Corneal Fluorescein Staining—Fluorescein stain (1% solution) was applied to the conjunctival sac. The surface of the cornea was examined using a dissecting microscope (Olympus SZX10, Waltham, MA). The scoring of staining was completed by a masked ophthalmologist, and scored 0 for no staining, score 1 for a quarter of staining, score of 2 for less than a half, score of 3 for half, and 4 for more than half of the eye.

Ocular Histology—At the conclusion of the study, the eyes were exenterated and fixed in 10% neutral buffered formalin Sections were prepared at approximately 5 μm and stained with Periodic Acid Schiff (PAS) in order to examine goblet cell density. Histological sections were scanned and quantified using a Zeiss Axio Scan. Z1 (Thornwood, NY) and Panoramic Viewer software (3D HISTECH Ltd.).

qRT-PCR—Total RNA was extracted from excised lacrimal glands using TRI-reagent (Molecular Research Center, Cincinnati, OH), and quantified using a NanoDrop 2000 (Thermo Scientific). For the reverse transcriptase assay, 2 μg RNA was converted to cDNA using a QuantiTect Reverse Transcription Kit (Qiagen, Valencia, CA). Quantitative real-time PCR was then performed using VeriQuest Probe qPCR Mastermix (Affymetrix, Santa Clara, CA), (Thermo Scientific) specific for (IFN-γ:Mm01168134_ml, FAM-MGB dye), (IL-1β:Mm00434228_ml, FAM-MGB dye), and (IL-6:Mm00446190_ml, FAM-MGB dye) (Gusb: Mm01197698_ml, VIC-MGB PL dye, endogenous control). Duplex reactions (target gene+GUSB) were run and analyzed on a StepOnePlus Real-Time PCR System (Applied Biosystems, Carlsbad, CA). Relative fold changes of IFN-γ, IL-6 and FoxP3 expression were calculated and normalized based upon the $2^{\Delta\Delta Ct}$ method, with the saline group as the untreated control.

Immunofluorescences of the lacrimal gland—At the end of the study, lacrimal glands were excised from the mice. Lacrimal glands were fixed with 4% PFA overnight, followed by cryoprotection through incubation in 30% sucrose overnight, and lastly embedded in O.C.T. medium. The cryosections were obtained at 7 μm thick and stained with fluorescent antibodies. Specifically, 7 μm sections were blocked with 5% normal donkey serum and 1% Tween20 in PBS. Blocked sections were incubated overnight at 4° C. with rat anti-FoxP3 (FJK-16s; eBio) and rabbit anti-CD3 (SP7, monoclonal rabbit IgG; Abcam, Cambridge, MA). The sections were then incubated with a secondary antibody, Alexa Fluor 594 donkey anti-rat IgG (ThermoFisher Scientific Waltham, MA) and Alexa Fluor 647 donkey anti-rabbit IgG (Jackson ImmunoResearch Laboratories, West Grove, PA) for 1 hour at room temperature and then mounted using Fluoroshield mounting medium with DAPI (Abcam, Cambridge, MA). The images were captured using a Zeiss Axio Scanner Z.1.

Statistical Analysis—Data expressed as mean±S.D. Comparisons between multiple treatment groups were performed using one-way ANOVA, followed by Bonferroni multiple comparisons, and $p \leq 0.05$ was considered statistically significant. The PCR data expressed as mean±SEM was analyzed utilizing a t-test with Welch correction, and $p \leq 0.05$ was considered statistically significant. Statistical tests were performed using GraphPad Prism Software 6.0 (GraphPad Prism, San Diego, CA)

Results

Characterization of TRI Microspheres: IL-2, TGF-β1 and Rapamycin

The TGF-β1 microspheres were formulated to avoid a 20-day initial lag phase of release. The formulation of TGF-β1 microspheres contains a PEG-PLGA diblock copolymer (4 wt %, Mn ~5 kDa), which accelerated release by increasing matrix swelling, and the ester-terminated PLGA helped to minimize the electrostatic interactions between the PLGA polymer and the positively charged protein.

After adapting the release of TGF-β1, the surface morphology of the microspheres were characterized using scanning electron microscopy (SEM). The SEM images show spherical PLGA based rapamycin microspheres while on the other hand, the IL-2 microspheres contained pores with a high initial burst followed by a slow continuous release for the length of the experimental study. Additionally, the newly fabricated TGF-β1 microspheres contained uneven surface morphology. Lastly, the average size of the fabricated TRI MS were examined using a Coulter Counter. The average sizes of the microspheres were 12 μm (rapamycin), 19 μm (IL-2), and 17 μm (TGF-β). (See FIGS. 14A-14I). Once the fabricated TRI MS were characterized the microspheres were utilized in an experimental inflammatory model of DED to determine their efficacy in preventing key features of the disease.

TRI Microspheres Prevent Key Signs of Dry Eye Disease

Figure 9:
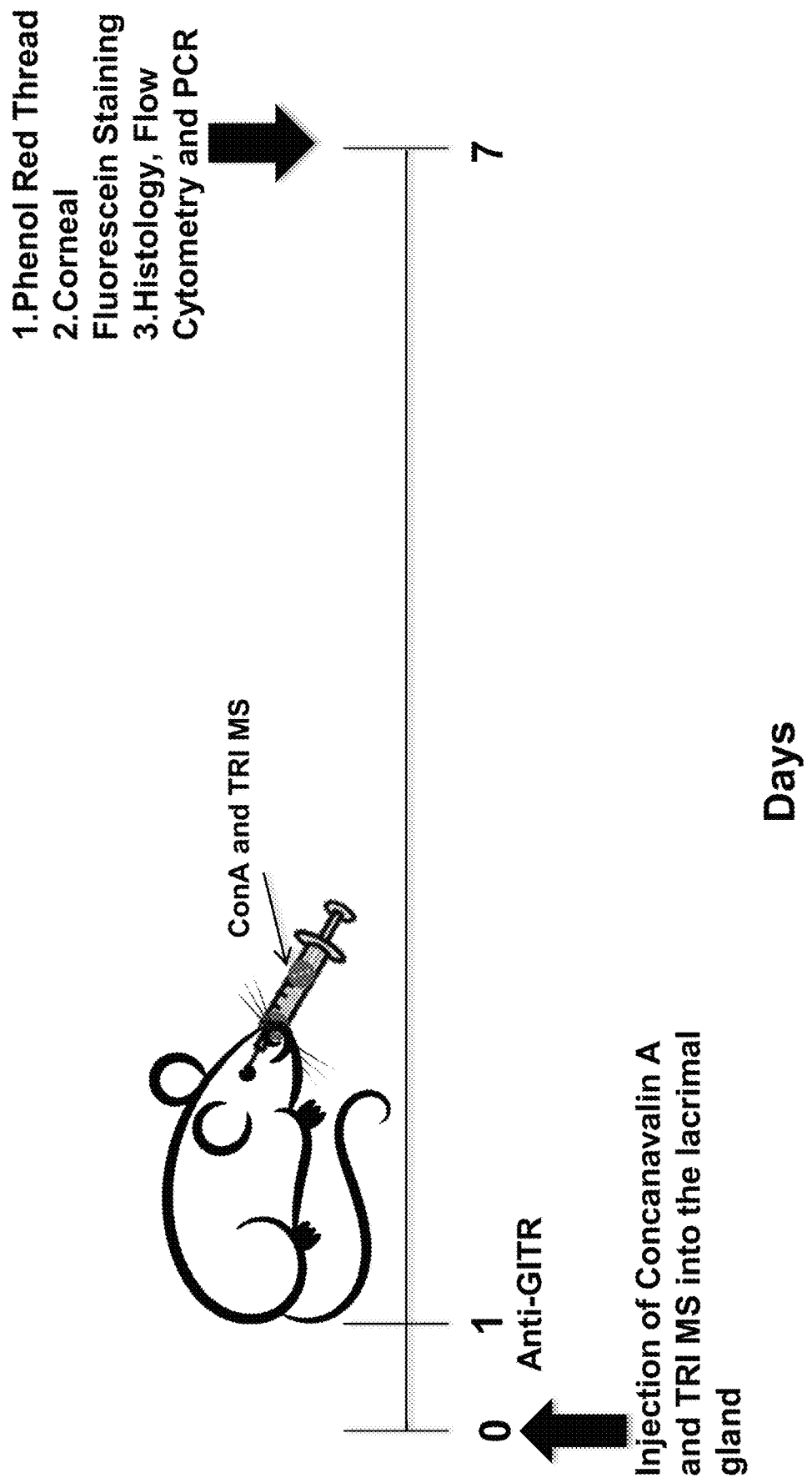
FIG. 9. TRI microspheres for the prevention of inflammation associated with Dry eye Disease (DED) in mice. A timeline for the experimental murine model of inflammation induce via Concanavalin A.

To investigate whether TRI MS were capable of preventing key signs of dry eye disease, aqueous tear secretion, goblet cell density, and corneal fluorescein staining were examined Concanavalin A (ConA) was injected into the lacrimal gland to induce DED, and for TRI MS or Blank MS treatment groups, MS were incorporated in ConA injections (FIG. 9). One week following the administration of ConA and the Blank or TRI MS, phenol red thread testing was performed to evaluate aqueous tear secretion. The administration of ConA (diseased) significantly reduced tear secretion as compared to an injection of saline (non-diseased) (FIG. 10A). Notably, tear secretion was restored to non-diseased levels in DED mice treated with TRI MS, while administration of Blank MS (unloaded) had no noticeable effect on tear production in diseased mice (FIG. 10A). To identify whether a single factor or a combination of factors was required to prevent loss of aqueous tear production, responses to treatment with single (ex: IL-2 MS) and double (ex: IL-2 MS and TGF-β1 MS) formulations were examined No individual MS formulation, or combination of two MS formulations, were able to restore tear production inhibited by ConA, suggesting that therapeutic efficacy required delivery of all three factors.

Due to the prevention of reduced tear secretion utilizing the combination of all three factors (TRI MS), we sought to investigate a key aspect associated with a healthy tear film. Specifically, an integral component of the tears known as mucin, which is produced by goblet cells found in the ocular tissue of the conjunctiva. Examination of the histological sections of the ocular tissue suggested that there was a significant loss in the density of Periodic Acid Schiff (PAS) stained goblet cells (pink/purple cells in conjunctiva epithelium layer) in the ConA as compared to the saline group (FIGS. 10B, 10C). Moreover, treatment with TRI MS led to maintenance of goblet cell density, unlike mice with ConA-induced DED (with or without Blank MS) (FIG. 10B). Overall, histological sections revealed that TRI MS treatment markedly inhibited the attenuation of goblet cells that generally contributes to an unstable tear film. Since aqueous tear and mucin production protects the corneal epithelium, it was determined whether the restoration of tear production and protection of mucin-producing goblet cells with TRI MS treatment also protected the integrity of the ocular surface.

Figure 11B:
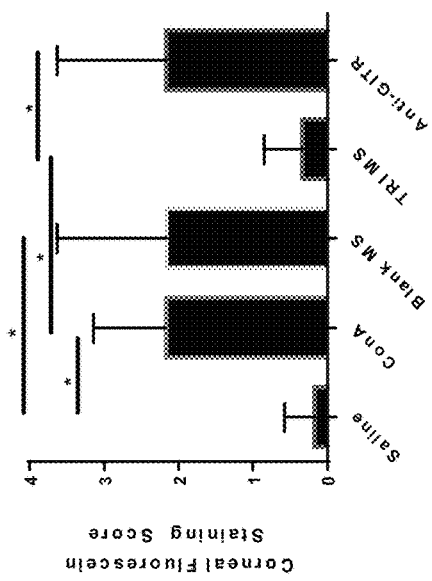
FIGS. 11A-11B. TRI MS reduce ocular surface staining (FIG. 11A) Representative images of corneal fluorescein staining.
Figure 11A:
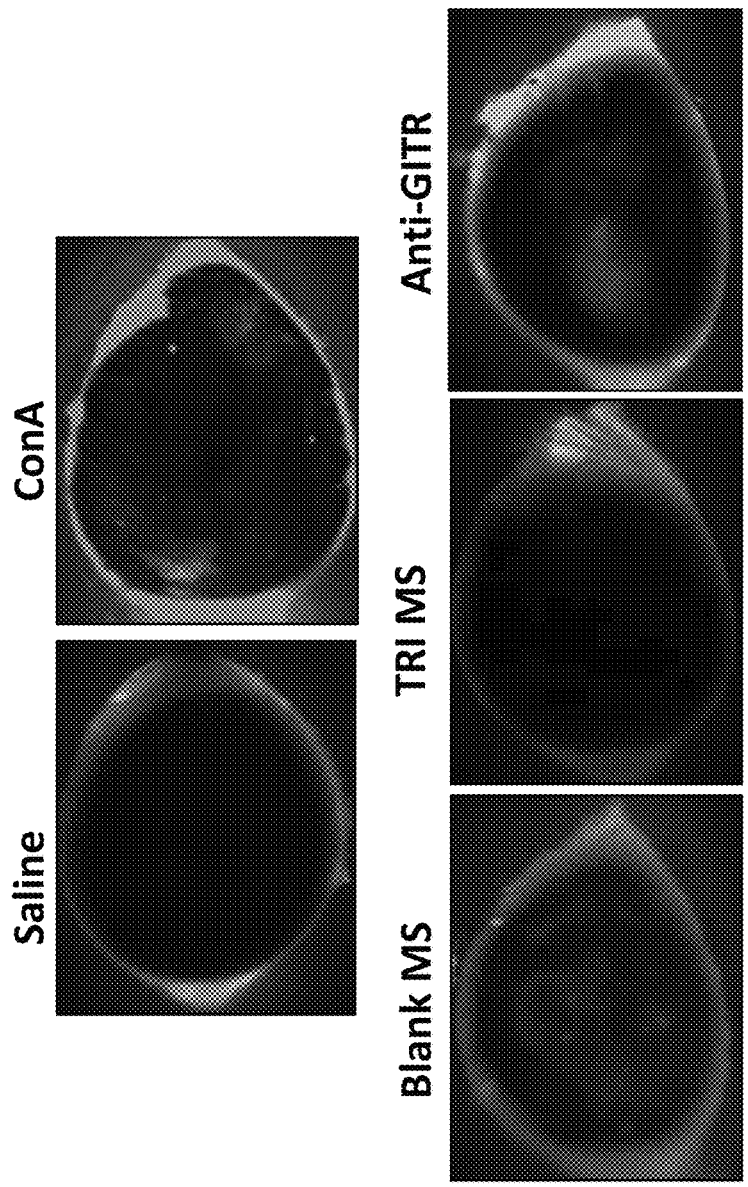

A healthy tear film has shown to correlate to the maintenance of the ocular surface. For this reason, ocular surface health was assessed using fluorescein staining, with the degree of punctate staining as an indicator of disease severity. Fluorescein images of the ocular surface were captured and scored by a masked ophthalmologist on a scale of 0 to 4, with 0 corresponding to no staining, and 4 corresponding to staining on more than 50% of the cornea, as seen in FIG. 11A. The ocular staining score was significantly lower for the saline and TRI MS groups as compared to the ConA and Blank MS groups (FIG. 11B). Eyes from mice treated with ConA plus single or double MS formulations were also examined. The representative scores suggest that there was a significant reduction of fluorescein staining for the rapamycin and TGF-β1 microspheres as compared to merely administering IL-2 microspheres. However, the single and double controls were unable to reduce ocular staining to the same extent as the TRI MS treatment. Collectively, the data suggest that the local administration of TRI MS prevented a loss of aqueous tear secretion, maintained goblet cells, and decreased ocular staining, consistent with amelioration of DED.

TRI MS Decrease Pro-Inflammatory Cytokines and Infiltration of T Lymphocytes

Figure 12:
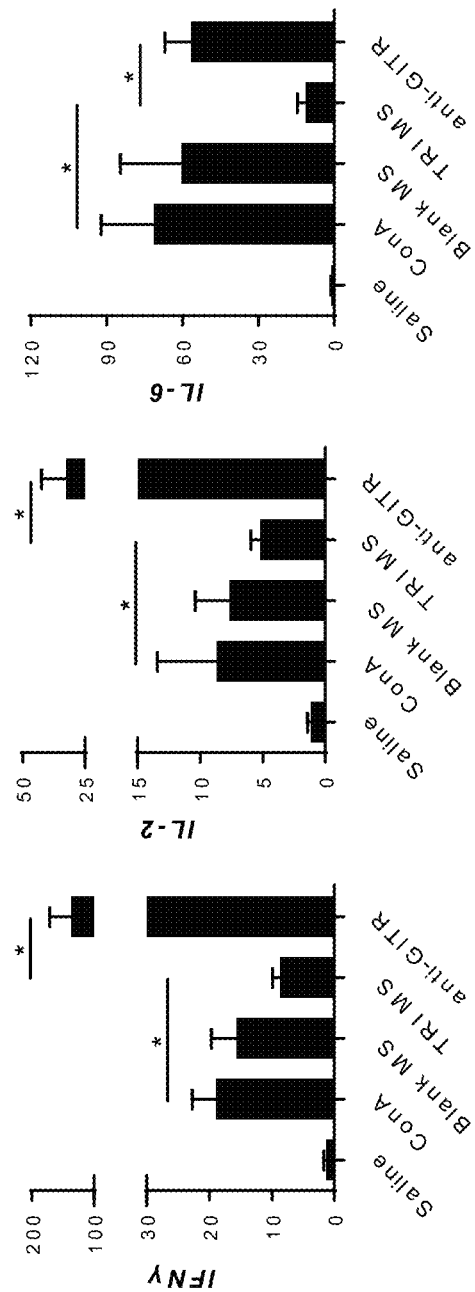
FIG. 12. Administration of TRI MS reduces levels of cytokines in the lacrimal gland shown as mean±SEM. * p≤0.05
Figure 14B:
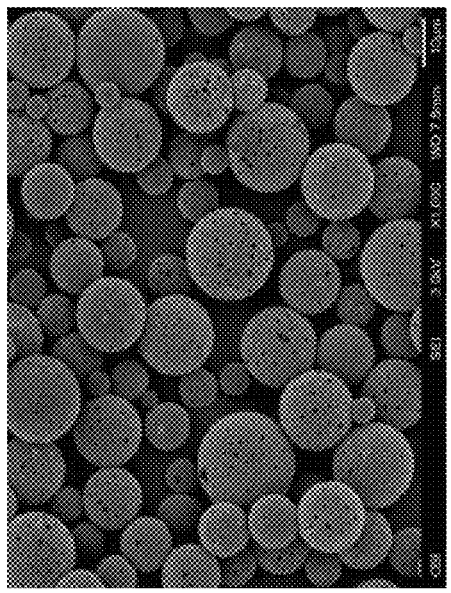
(FIG. 14D) Release Kinetics of Rapamycin Microspheres is shown (n=3) (FIG. 14E) Release Kinetics of porous IL-2 Microspheres (n=3) (FIG. 14F) Release Kinetics of TGF-β1 Microspheres (n=3).
(FIG. 14G) Size distribution of Rapamycin Microspheres (FIG. 14H) Size distribution of IL-2 Microspheres (FIG. 14I) Size Distribution of TGF-β1 Microspheres
Figure 14C:
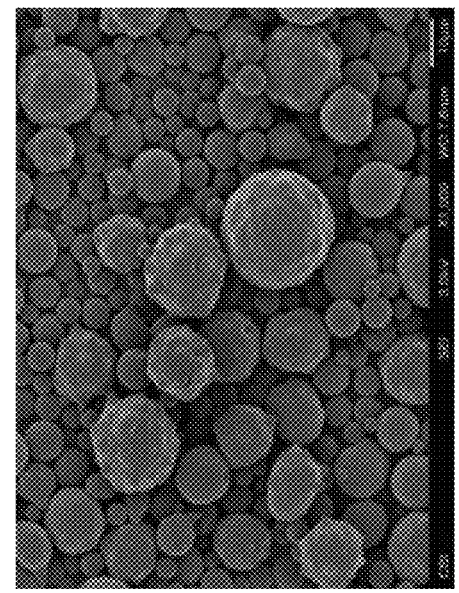
Figure 14A:
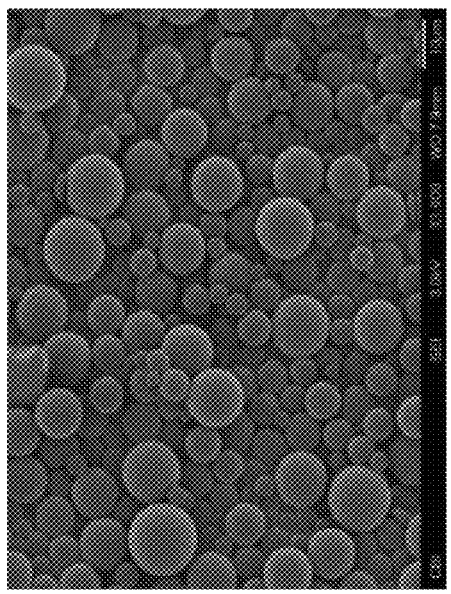
Figure 14D:
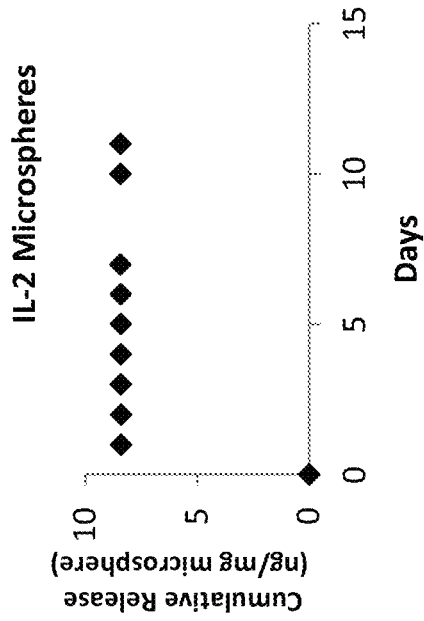
Figure 14E:
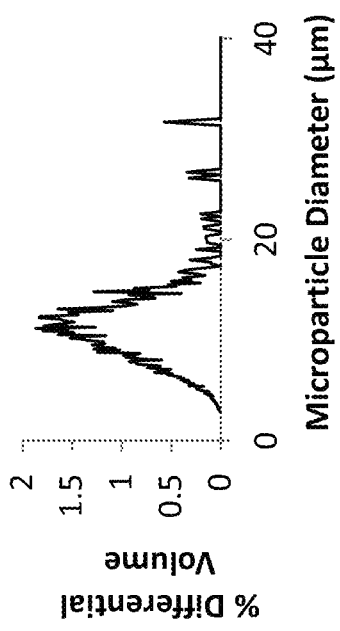
Figure 14F:
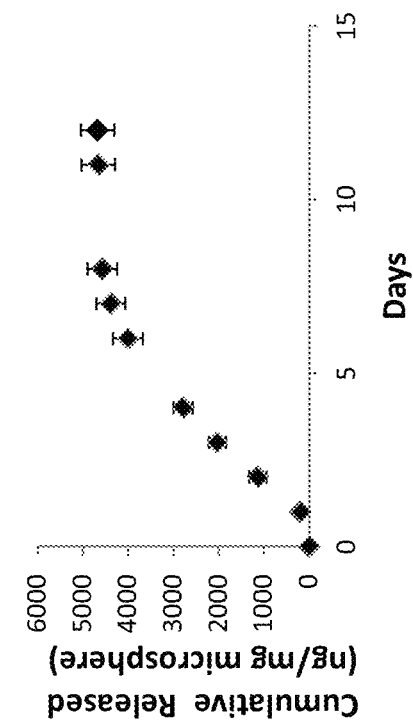
Figure 14G:
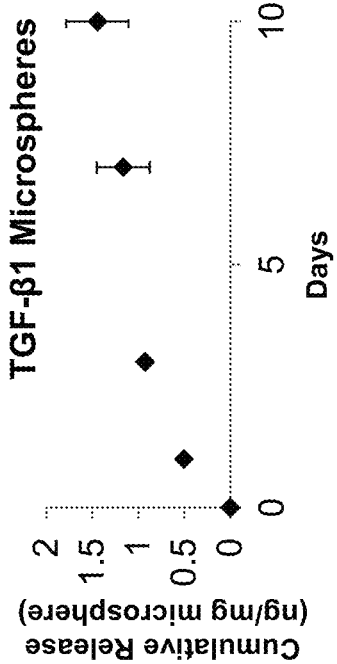
Figure 14I:
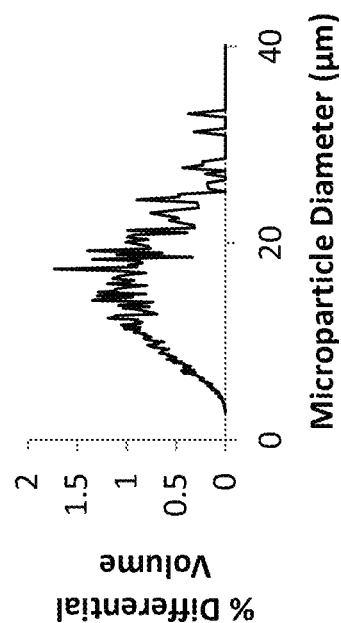
Figure 14H:
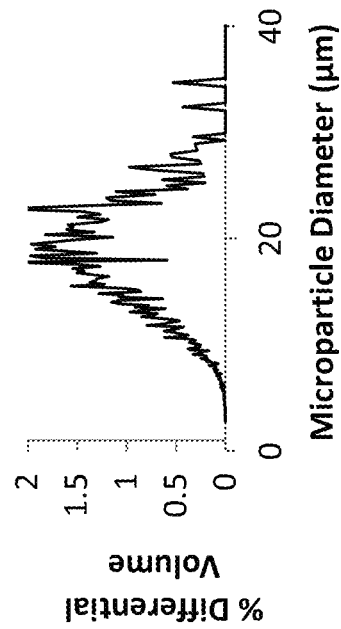

The local milieu of the lacrimal glands was examined to identify whether the TRI MS altered the underlying immune response that ultimately prevented symptoms of DED. Specifically, the levels of pro-inflammatory cytokines was investigated. Notably, there was a significant reduction of IFN-γ, IL-6, and IL-2 in the lacrimal gland of the TRI MS group, compared to the ConA (FIG. 12). The increase of pro-inflammatory cytokine expression correlated to an increase of CD4+ T cells in the diseased groups as compared to the TRI MS treated group (FIG. 13). Together this data suggests that the TRI MS treatment was able to inhibit the ConA-induced pro-inflammatory microenvironment in the lacrimal gland tissue.

Suppression of Tregs Via Administration of Anti-GITR

To confirm that Tregs were involved in suppressing the signs associated with DED, an agnostic antibody (DTA-1) specific for GITR (glucocorticoid tumor necrosis factor) was administered 1 day after the injection of the ConA and TRI MS. Monoclonal antibody anti-GITR (DTA-1) acts to systemically attenuate the suppressive function of Tregs by inhibiting the ability of conventional T cells to be suppressed by Tregs. Mice administered anti-GITR, prior to ConA and TRI MS, developed key pathological features of dry eye disease as indicated by the decrease of aqueous tear secretion, reduction of goblet cells in the conjunctiva, and the increase in fluorescein staining as compared to the TRI MS group. Moreover, with the administration of anti-GITR, levels of pro-inflammatory cytokines were significantly increased as compared to the TRI MS. Overall, anti-GITR was utilized to suppress the function of Tregs, and negated any therapeutic effects seen with TRI MS alone. This evidence could potentially suggest that the therapeutic effects of TRI MS would be dependent on functional Tregs.

TRI MS Reduce the Proliferation of T-Cells within the Lacrimal Gland

In order to examine the local immune environment of T-cells in the lacrimal gland, immunofluorescence staining on lacrimal glands was completed in order to identify CD3+ T cells in the tissue Immunofluorescence staining with anti-CD3 and Foxp3 monoclonal antibodies was performed on cryosections of lacrimal glands on the diseases, non-diseased, blank microspheres and TRI MS groups. CD3+ T cells were observed in the lacrimal gland of the diseased, blank microspheres and TRI MS groups. Representative images suggest that there is an overall lower amount of T-cells in TRI MS as compared to diseased group, suggesting that the TRI MS are restoring the immunological homeostasis in the lacrimal gland.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating an ocular disorder in a subject comprising administering a therapeutic agent-loaded carrier to an ocular site of the subject in need thereof, wherein the therapeutic agent loaded-carrier provides controlled delivery of the therapeutic agent under conditions suitable for recruiting regulatory T cells to an ocular region of interest or inducing regulatory T cells in an ocular region of interest, wherein the ocular disorder is dry eye disease and the therapeutic agent is CCL22.

2. The method of claim 1, wherein the regulatory T cells are endogenous.

3. The method of claim 1, wherein the therapeutic agent-loaded carrier is in the form of therapeutic agent-loaded microparticles.

4. The method of claim 1, wherein the therapeutic agent-loaded carrier comprises therapeutic agent-loaded microparticles.

5. The method of claim 3, wherein the microparticles comprise poly (lactic-co-glycolic acid).

6. The method of claim 1, wherein the method provides controlled release under conditions to provide a concentration gradient within or near the ocular disorder site.

7. The method of claim 3, wherein the therapeutic agent-loaded microparticles are included in a composition that does not include a hydrogel.

8. The method of claim 1, wherein the method comprises recruiting regulatory T cells to an ocular region of interest.

9. The method of claim 1, wherein the method comprises inducing regulatory T cells in an ocular region of interest.

10. The method of claim 1, wherein the therapeutic agent-loaded carrier is not administered with a hydrogel.

* * * * *